US007569386B2

(12) United States Patent
DeAngelis

(10) Patent No.: US 7,569,386 B2
(45) Date of Patent: Aug. 4, 2009

(54) CHONDROITIN SYNTHASE GENE AND METHODS OF MAKING AND USING SAME

(75) Inventor: Paul L. DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 656 days.

(21) Appl. No.: 11/042,530

(22) Filed: Jan. 24, 2005

(65) Prior Publication Data

US 2005/0164984 A1 Jul. 28, 2005

Related U.S. Application Data

(63) Continuation of application No. 09/842,484, filed on Apr. 25, 2001, now abandoned, application No. 11/042,530, filed on Jan. 24, 2005, and a continuation-in-part of application No. 09/283,402, filed on Apr. 1, 1999, now abandoned, and a continuation-in-part of application No. 09/437,277, filed on Nov. 10, 1999, now Pat. No. 6,444,447.

(60) Provisional application No. 60/199,538, filed on Apr. 25, 2000.

(51) Int. Cl.
*C12N 5/10* (2006.01)
*C12N 1/21* (2006.01)
*C12N 9/10* (2006.01)
*C07H 21/04* (2006.01)

(52) U.S. Cl. ............... 435/325; 435/252.3; 435/254.11; 435/320.1; 536/23.2

(58) Field of Classification Search ....................... None
See application file for complete search history.

(56) References Cited

U.S. PATENT DOCUMENTS

| | | | |
|---|---|---|---|
| 4,585,754 | A | 4/1986 | Meisner et al. |
| 4,990,601 | A | 2/1991 | Skjak-Braek et al. |
| 5,008,253 | A | 4/1991 | Casu et al. |
| 2003/0100534 | A1 | 5/2003 | Zoppetti et al. |

FOREIGN PATENT DOCUMENTS

| | | |
|---|---|---|
| EP | 00300035 | 5/1995 |
| EP | 01304338 | 4/2003 |
| WO | WO 00/27437 | 5/2000 |
| WO | WO 01/02597 | 1/2001 |
| WO | WO 01/80810 | 11/2001 |
| WO | WO 03/012099 | 2/2003 |

OTHER PUBLICATIONS

"Genetic Mapping of the K1 and K4 Antigens (L) of *Escherichia coli*. Non-Allelism of K(L) Antigens With K Antigens of 08:K27(A), 08:K8 (L) and 09:K57 (B)", Orskov et al., Acta Pathol Microbiol Scand B, 84:125-131 (1976).

"A Terminal 6-Sulfotransferase Catalyzing A Synthesis of N-Acetylgalactosamine 4,6-Bissulfate Residue At The Nonreducing Terminal Position of Chondroitin Sulfate" Nakanishi et al. The Journal of Biological Chemistry 1981, 256 (11) 5443-5449).

"Differences in the Effects of pH on the Hydrolytic and Transgalactosylic Reactions of Beta-Galactosidase (*Escherichia coli*)", Huber et al., Can. J. Biochem. Cell Biol., 61:198-206 (1983).

"Binding and Reactivity at the 'Glucose' Site of Galactosyl-Beta-Galactosidase (*Escherichia coli*)", Huber et al., Arch Biochem Biophys., 234: 151-160 (1984).

"Effect of Replacing Uridine 33 in Yeast tRNAPhe on the Reaction With Ribosomes", Dix et al., J. Biol. Chem., 261(22):10112-8 (1986).

"Structure and Serological Characteristics of the Capsular K4 Antigen of *Escherichia coli* O5:K4:H4, A Fructose-Containing Polysaccharide With a Chondroitin Backbone", Rodriguez et al., Eur. J. Biochem., 177:117-124 (1988).

"The Carboxy-Terminal Domain of the LexA Repressor Oligomerises Essentially as the Entire Protein", Schnarr et al., FEBS Lett., 234:56-60 (1988).

"A Cryptic Fimbrial Gene in Serratia Marcescens", Moriya et al., J. Bacteriol., 171(12): 6629-36 (1989).

"Monoclonal Antibodies Specific for K88ab, K88ac and K88ad Antigens of *Escherichia coli*", Li et al., Wei Sheng Wu Xue Bao, 29:348-353 (1989) (Full Article Unavailable; Abstract Only).

"Kinetic Characterization of the Unisite Catalytic Pathway of Seven Beta-Subunit Mutant F1-ATPases From *Escherichia coli*", al-Shawi et al., J. Biol. Chem., 264(26): 15376-83 (1989).

"Slow-Binding Inhibition of the *Escherichia coli* Pyruvate Dehydrogenase Multienzyme Complex by Acetylphosphinate", Schonbrunn-Hanebeck et al., Biochemistry, 29(20): 4880-5 (1990).

"Molecular Cloning and Expression of the Genes Encoding the *Escherichia coli* K4 Capsular Polysaccharide, A Fructose-Substituted Chondroitin", Drake et al., FEMS Microbiol. Lett., 54(1-3):227-30 (1990) (Full Article Unavailable; Abstract Only).

"Electron Microscopic Study of Coexpression of Adhesive Protein Capsules and Polysaccharide Capsules in *Escherichia coli*", Kronke et al., Infect. Immunity, 58:2710-4 (1991).

"Transport and Utilization of Ferrioxamine-E-Bound Iron in Erwinia Herbicola (Pantoea agglomerans)", Matzanke et al., Biol. Met., 181-185 (1991).

"Modulation of the Tight Binding of Carboxyarabinitol 1, 5-Biphosphate to the Large Subunit of Ribulose 1,5-Bisphosphate Carboxylase/Oxygenase", Smrcka et al., Arch. Biochem. Biophys., 286: 14-9 (1991).

"Slow-Onset Inhibition of Ribosomal Peptidyltransferase by Lincomycin", Kallia-Raftopoulos et al., Arch. Biochem. Biophys., 298: 332-339 (1992).

(Continued)

*Primary Examiner*—Nashaat T Nashed
*Assistant Examiner*—Md. Younus Meah
(74) *Attorney, Agent, or Firm*—Dunlap Codding, P.C.

(57) ABSTRACT

The present invention relates to a chondroitin synthase gene and methods of making and using same. In more particular, but not by way of limitation, the present invention relates to a chondroitin synthase gene from *Pasteurella multocida* and methods of isolating and using same. Additionally, the present invention relates to the use of unsulfated chondroitin and its preparation, as well as conversion into modified versions such as dermatan sulfate and chondroitin sulfate polymers.

16 Claims, 10 Drawing Sheets

OTHER PUBLICATIONS

"Enhanced Catalysis by Active-Site Mutagenesis at Aspartic Acid 153 in *Escherichia coli* Alkaline Phosphatase", Matlin et al., Biochemistry, 31(35): 8196-8200 (1992).
"A Study of Vitamin Inhibition on the Mutagenicity of the Antineoplastic Drugs", Zhao and Huang, Zhonghua Yu Fang Yi Xue Za Zhi, 26:291-293 (1992) (Full Article Unavailable; Abstract Only).
"Molecular Cloning of a Gene Coding for Beta-Glucanase From Bacillus Subtilis K4, Antagonist to Plant Pathogenic Fungi", Kim et al., RDA Journal of Agricultural Science Biotechnology, 35(1): 213-218 (1993).
"Preliminary Study of Test Methods to Assess the Virucidal Activity of Skin Disinfectants Using Poliovirus and Bacteriophages", Davies et al., Journal of Hospital Infection, 25(2): 125-131 (1993).
"*The Escherichia coli* serA-Linked Capsule Locus and its Flanking Sequences are Polymorphic, Genetic Evidence for the Existence of More Than Two Groups of Capsule Gene Clusters", Drake et al., J. Gen. Microbiol., 139 (Pt. 8): 1707-1714 (1993).
"Reaction of Modified and Unmodified tRNA (Tyr) Substrates With Tyrosyl-tRNA Synthetase (*Bacillus stearothermophilus*)", Avis et al., Biochemistry, 32(20): 5312-5320 (1993).
"Effect of pH on Solubility and Ionic State of Lipopolysaccharide Obtained From the Deep Rough Mutant of *Escherichia coli*", Din et al., Biochemistry, 32(17): 4579-4586 (1993).
"Amino Acid Residues of the Kringle-4 and Kringle-5 Domains of Human Plasminogen That Stabilize Their Interactions With Omega-Amino Acid Ligands", McCance et al., J. Biol. Chem., 269(51):32405-32410 (1994).
"Kinetic Mechanism of Kinesin Motor Domain", Ma and Taylor, Biochemistry, 34(40): 13233-13241 (1995).
"Production and Purification of an Extracellularly Produced K4 Polysachharide From *Escherichia coli*", Manzoni et al., Biotechnol. Lett., 18(4): 383-386 (1996).
"A Novel Family of Phospholipase D Homologues That Includes Phospholipid Synthases and Putative Endonucleases: Identification of Duplicated Repeats and Potential Active Site Residues", Ponting and Kerr, Protein Science, 914-922 (May 1996).
"Biosynthesis of Dermatan Sulphate. Defructosylated *Escherichia coli* K4 Capsular Polysaccharide as a Substrate for the D-Glucuronyl C-5 Epimerase, and an Indication of a Two-Base Reaction Mechanism", Hannesson et al., Biochem. J., 313(Pt. 2): 589-596 (1996).
"Biosynthesis of the *Escherichia coli* K4 Capsule Polysaccharide: A Parallel System for Studies of Glycosyltransferases in Chondroitin Formation", Lidholt et al., J. Biol. Chem., 272(5):2682-2687 (1997).
"Kinetic Mechanism of Monomeric Non-Claret Disjunctional Protein (Ncd) ATPase", Pechatnikova et al., J. Biol. Chem., 272(49): 30735-30740 (1997).
"A Two-Site Mechanism for ATP Hydrolysis by the Asymmetric Rep Dimer P2S as Revealed by Site-Specific Inhibition With ADP-A1F4", Wong and Lohman, Biochemistry, 36(11): 3115-3125 (1997).
"The Capsule Biosynthetic Locus of Pasturella Multocida A:1", Chung et al., FEMS Microbiology Letters, 186:289-296 (1998).
"Role of Fimbriae-Mediated Adherence for Neutrophil Migration Across *Escherichia coli*-Infected Epithelial Cell Layers", Godaly et al., Molecular Microbiology, 30(4): 725-735 (1998).
"Complete Kinetic Mechanism of Elongation Factor Tu-Dependent Binding of Aminoacyl-tRNA to the a Site of the *E. coli* Ribosome", Pape et al., EMBO J., 17(24): 7490-7497 (1998).
"Transfer RNA Identity Contributes to Transition State Stabilization During Aminoacyl-tRNA Synthesis", Ibba et al., Nucleic Acids Research, 27(18):3631-3637 (1999).
"Contractile Function and Myoplasmic Free Ca2+ (Cam) in Coronary and Mesenteric Arteries of Endotoxemic Guinea Pigs", Jones et al., Shock, 11: 64-71 (1999).
"Kinetic Studies on the Interaction Between a Ribosomal Complex Active in Peptide Bond Formation and the Macrolide Antibiotics Tylosin and Erythromycin", Dinos et al., Biochemistry, 39(38): 11621-11628 (2000).
"Structure-Function Relationships in Novel Peptide Dodecamers With Broad-Spectrum Bactericidal and Endotoxin-Neutralizing Activities", Mayo et al., Biochemical Journal, 349(3): 717-728 (2000).
Identification and Molecular Cloning of a Chondroitin Synthase From Pasteurella Multocida Type F, Paul DeAngelis, et al., Journal of Biological Chemistry, vol. 275, No. 31, pp. 24124-24129, Apr. 2000.
"Ring Opening is not Rate-Limiting in the GTP Cyclohydrolase I Reaction", Bacher et al., J. Biol. Chem., 276(4): 2622-2626 (2001).
"Subunit Communication in Tetrameric Class 2 Human Liver Aldehyde Dehydrogenase as the Basis for Half-Of-The-Site Reactivity and the Dominance of the Oriental Subunit in a Heterotetramer", Weiner et al., Chemico-Biological Interactions, 130-132(1-3):47-56 (2001).
Molecular Cloning and Expression of a Human Chondroitin Synthase, Hiroshi Kitagawa, et al., Journal of Biological Chemistry, vol. 276, No. 42, pp. 38721-38726, August 2001.
Utility of Molecularly Dissected Synthases for Chemoenzymatic Synthesis of Glycosaminoglycan Oligosaccharides, Paul DeAngelis, Glycobiology, vol. 11, No. 10, pp. 934, Oct. 2001.
"Detection of Submicrogram Quantitites of Glycosaminoglycans on Agarose Gels by Sequential Staining With Toluidine Blue and Stains-All", Volpi and Maccari, Electrophoresis, 23(24):4060-4066 (2002).
Keratan Sulfate Biosynthesis, James Funderburgh, IUBMB Life, vol. 54, pp. 187-194, 2002.
Mammalian Hyaluronan Synthases, Naoki Itano, et al., IUBMB Life, vol. 54, pp. 195-199, 2002.
Molecular Cloning and Expression of Human Chondroitin N-Acetylgalactosaminyltransferase, Toru Uyama, et al. Journal of Biological Chemistry, vol. 277, No. 11, pp. 8841-8846, Jan. 2002.
Molecular Cloning and Characterization of Chondroitin Polymerase From *Escherichia coli* Strain K4, Toshio Ninomiya, et al., Journal of Biological Chemistry, vol. 277, No. 24, pp. 21567-21575, Apr. 2002.
Molecular Cloning and Characterization of a Novel Chondroitin Sulfate Glucuronyltransferase That Transfers Glucuronic Acid to N-Acetylgalactosamine, Masanori Gotoh, et al., Journal of Biological Chemistry, vol. 277, No. 41, pp. 38179-38188, Jul. 2002.
Structure Function Analysis of Pasteurella Glycosaminoglycan Synthesis, Wei Jing, et al., Glycobiology, vol. 12, No. 10, pp. 705, Oct. 2002.
Biosynthesis of Chondroitin/Dermatan Sulfate, Jeremiah Silbert, et al., IUBMB Life, vol. 54, pp. 177-186, Oct. 2002.
Functional Characteristics and Catalytic Mechanisms of the Bacterial Hyaluronan Synthases, Paul Weigel, IUBMB Life, vol. 54, pp. 201-211, Oct. 2002.
"Structural/Functional Characterization of the Alpha 2-Plasmin Inhibitor C-Terminal Peptide", Frank et al., Biochemistry, 42:1078-1085 (2003).
"Trp-999 of Beta-Galactosidase (*Escherichia coli*) is a Key Residue for Binding, Catalysis, and Synthesis of Allolactose, the Natural Lac Operon Inducer", Huber et al., Biochemistry, 42(6): 1796-1803 (2003).
"Separation of Capsular Polysaccharide K4 and Defructosylated K4 Derived Disaccharides by High-Performance Capillary Electrophoresis and High-Performance Liquid Chromatography", Volpi, Electrophoresis, 24(6): 1063-1068 (2003).
"Milligram-Scale Preparation and Purification of Oligosaccharides of Defined Length Possessing the Structure of Chondroitin From Defructosylated Capsular Polysaccharide K4", Volpi, Glycobiology, 13(9):635-640 (2003).

```
            1                                                     50
     PmCS   MNTLSQAIKA YNSNDYELAL KLFEKSAETY GRKIVEFQII KCKEKLSTNS
    PmHAS   MNTLSQAIKA YNSNDYQLAL KLFEKSAEIY GRKIVEFQIT KCKEKLSAHP
Consensus   MNTLSQAIKA YNSNDY#LAL KLFEKSAEiY GRKIVEFQIi KCKEKLSanp

            51                                                   100
     PmCS   YVS....... EDKKNSVCDS SLDIATQLLL SNVKKLTLSE SEKNSLKNKW
    PmHAS   SVNSAHLSVN KEEKVNVCDS PLDIATQLLL SNVKKLVLSD SEKNTLKNKW
Consensus   sVn....... e#eKnnVCDS pLDIATQLLL SNVKKLtLS# SEKNsLKNKW

            101                                                  150
     PmCS   KSITGKKSEN AEIRKVELVP KDFPKDLVLA PLPDHVNDFT WYKNRKKSLG
    PmHAS   KLLTEKKSEN AEVRAVALVP KDFPKDLVLA PLPDHVNDFT WYKKRKKRLG
Consensus   KliTeKKSEN AE!RaVaLVP KDFPKDLVLA PLPDHVNDFT WYKnRKKrLG

            151                                                  200
     PmCS   IKPVNKNIGL SIIIPTFNRS RILDITLACL VNQKTNYPFE VVVADDGSKE
    PmHAS   IKPEHQHVGL SIIVTTFNRP AILSITLACL VNQKTHYPFE VIVTDDGSQE
Consensus   IKPenqn!GL SII!pTFNRp aILdITLACL VNQKTnYPFE V!VaDDGSqE

            201                                                  250
     PmCS   NLLTIVQKYE QKLDIKYVRQ KDYGYQLCAV RNLGLRTAKY DFVSILDCDM
    PmHAS   DLSPIIRQYE NKLDIRYVRQ KDNGFQASAA RNMGLRLAKY DFIGLLDCDM
Consensus   #LlpI!rqYE #KLDIrYVRQ KDnG%QacAa RN$GLRlAKY DF!giLDCDM
```

Fig. 1a

```
           251                                                 300
     PmCS  APQQLWVHSY LTELLEDNDI VLIGPRKYVD THNITAEQFL NDPYLIESLP
    PmHAS  APNPLWVHSY VAELLEDDDL TIIGPRKYID TQHIDPKDFL NNASLLESLP
Consensus  AP#qLWVHSY laELLED#Di tiIGPRKY!D TqnIdae#FL N#asLiESLP

           301                                                 350
     PmCS  ETATNNNPSI TSKGNISLDW RLEHFKKTDN LRLCDSPFRY FSCGNVAFSK
    PmHAS  EVKTNNSVAA KGEGTVSLDW RLEQFEKTEN LRLSDSPFRF FAAGNVAFAK
Consensus  EtaTNNnpaa kgeGn!SLDW RLEqFeKT#N LRLcDSPFR% FaaGNVAFaK

           351                                                 400
     PmCS  EWLNKVGWFD EEFNHWGGED VEFGYRLFAK GCFFRVIDGG MAYHQEPPGK
    PmHAS  KWLNKSGFFD EEFNHWGGED VEFGYRLFRY GSFFKTIDGI MAYHQEPPGK
Consensus  eWLNKsGfFD EEFNHWGGED VEFGYRLFak GcFFrtIDGg MAYHQEPPGK

           401                                                 450
     PmCS  ENETDREAGK SITLKIVKEK VPYIYRKLLP IEDSHIHRIP LVSIYIPAYN
    PmHAS  ENETDREAGK NITLDIMREK VPYIYRKLLP IEDSHINRVP LVSIYIPAYN
Consensus  ENETDREAGK nITLdImrEK VPYIYRKLLP IEDSHInR!P LVSIYIPAYN

           451                                                 500
     PmCS  CANYIQRCVD SALNQTVVDL EVCICNDGST DNTLEVINKL YGNNPRVRIM
    PmHAS  CANYIQRCVD SALNQTVVDL EVCICNDGST DNTLEVINKL YGNNPRVRIM
Consensus  CANYIQRCVD SALNQTVVDL EVCICNDGST DNTLEVINKL YGNNPRVRIM
```

Fig. 1b

```
           501                                                550
     PmCS  SKPNGGIASA SNAAVSFAKG YYIGQLDSDD YLEPDAVELC LKEFLKDKTL
    PmHAS  SKPNGGIASA SNAAVSFAKG YYIGQLDSDD YLEPDAVELC LKEFLKDKTL
Consensus  SKPNGGIASA SNAAVSFAKG YYIGQLDSDD YLEPDAVELC LKEFLKDKTL

           551                                                600
     PmCS  ACVYTTNRNV NPDGSLIANG YNWPEFSREK LTTAMIAHHF RMFTIRAWHL
    PmHAS  ACVYTTNRNV NPDGSLIANG YNWPEFSREK LTTAMIAHHF RMFTIRAWHL
Consensus  ACVYTTNRNV NPDGSLIANG YNWPEFSREK LTTAMIAHHF RMFTIRAWHL

           601                                                650
     PmCS  TDGFNENIEN AVDYDMFLKL SEVGKFKHLN KICYNRVLHG DNTSIKKLGI
    PmHAS  TDGFNEKIEN AVDYDMFLKL SEVGKFKHLN KICYNRVLHG DNTSIKKLGI
Consensus  TDGFNEnIEN AVDYDMFLKL SEVGKFKHLN KICYNRVLHG DNTSIKKLGI

           651                                                700
     PmCS  QKKNHFVVVN QSLNRQGINY YNYDKFDDLD ESRKYIFNKT AEYQEEMDIL
    PmHAS  QKKNHFVVVN QSLNRQGITY YNYDEFDDLD ESRKYIFNKT AEYQEEIDIL
Consensus  QKKNHFVVVN QSLNRQGInY YNYDeFDDLD ESRKYIFNKT AEYQEEiDIL

           701                                                750
     PmCS  KDLKLIQNKD AKIAVSIFYP NTLNGLVKKL NNIIEYNKNI FVIILHVDKN
    PmHAS  KDIKIIQNKD AKIAVSIFYP NTLNGLVKKL NNIIEYNKNI FVIVLHVDKN
Consensus  KDiKiIQNKD AKIAVSIFYP NTLNGLVKKL NNIIEYNKNI FVI!LHVDKN
```

Fig. 1c

```
           751                                                 800
PmCS       HLTPDIKKEI LAFYHKHQVN ILLNNDISYY TSNRLIKTEA HLSNINKLSQ
PmHAS      HLTPDIKKEI LAFYHKHQVN ILLNNDISYY TSNRLIKTEA HLSNINKLSQ
Consensus  HLTPDIKKEI LAFYHKHQVN ILLNNDISYY TSNRLIKTEA HLSNINKLSQ

           801                                                 850
PmCS       LNLNCEYIIF DNHDSLFVKN DSYAYMKKYD VGMNFSALTH DWIEKINAHP
PmHAS      LNLNCEYIIF DNHDSLFVKN DSYAYMKKYD VGMNFSALTH DWIEKINAHP
Consensus  LNLNCEYIIF DNHDSLFVKN DSYAYMKKYD VGMNFSALTH DWIEKINAHP

           851                                                 900
PmCS       PFKKLIKTYF NDNDLRSMNV KGASQGMFMK YALPHELLTI IKEVITSCQS
PmHAS      PFKKLIKTYF NDNDLKSMNV KGASQGMFMT YALAHELLTI IKEVITSCQS
Consensus  PFKKLIKTYF NDNDLrSMNV KGASQGMFMk YALaHELLTI IKEVITSCQS

           901                                                 950
PmCS       IDSVPEYNTE DIWFQFALLI LEKKTGHVFN KTSTLTYMPW ERKLQWTNEQ
PmHAS      IDSVPEYNTE DIWFQFALLI LEKKTGHVFN KTSTLTYMPW ERKLQWTNEQ
Consensus  IDSVPEYNTE DIWFQFALLI LEKKTGHVFN KTSTLTYMPW ERKLQWTNEQ

           951                    972
PmCS       IQSAKKGENI PVNKFIINSI TL
PmHAS      IESAKRGENI PVNKFIINSI TL
Consensus  I#SAKrGENI PVNKFIINSI TL
```

Fig. 1d

NMR of Type F Polymer

CHONDROITIN SYNTHASE GENE AND METHODS OF MAKING AND USING SAME

CROSS-REFERENCE TO RELATED APPLICATIONS

This application is a continuation of U.S. patent application Ser. No. 09/842,484 filed Apr. 25, 2001 now abandoned and entitled CHONDROITIN SYNTHASE GENE AND METHODS OF MAKING AND USING SAME; is related to U.S. provisional application Ser. No. 60/199,538 filed Apr. 25, 2000 and entitled "POLYMER FORMATION AND RECOGNITION MECHANISMS AND METHODS OF MAKING AND USING SAME"; is a continuation-in-part of U.S. patent application Ser. No. 09/283,402, filed Apr. 1, 1999 now abandoned and entitled "DNA ENCODING HYALURONAN SYNTHASE FROM PASTEURELLA MULTOCIDA AND METHODS OF USE"; and is a continuation-in-part of U.S. patent application Ser. No. 09/437,277, filed Nov. 10, 1999 now U.S. Pat. No. 6,444,447 and entitled "POLYMER GRAFTING BY POLYSACCHARIDE SYNTHASES."

STATEMENT REGARDING FEDERALLY FUNDED RESEARCH

The government owns certain rights in the present invention pursuant to a grant from the National Institutes of Health (GM56497) and a grant from the National Science Foundation (MCB-9876193).

BACKGROUND OF THE INVENTION

1. Field of the Invention

The present invention relates to a chondroitin synthase gene and methods of making and using same. In more particular, but not by way of limitation, the present invention relates to a chondroitin synthase gene from *Pasteurella multocida* and methods of isolating and using same. Additionally, the present invention relates to the use of unsulfated chondroitin and its preparation, as well as conversion into modified versions such as dermatan sulfate and chondroitin sulfate polymers.

2. Background Information Relating to the Invention

Glycosaminoglycans [GAGs] are long linear polysaccharides consisting of disaccharide repeats that contain an amino sugar and are found in most animals. Chondroitin [β(1,4)GlcUA-β(1,3)GalNAc]$_n$, heparin/heparan [α1,4)GlcUA-[β(1,4)GlcNAc]$_n$, and hyaluronan [β(1,4)GlcUA-β(1,3)GlcNAc]$_n$ are the three most prevalent GAGs found in humans. Chondroitin and heparin typically have n=20 to 100, while hyaluronan typically has n=$10^3$. Chondroitin and heparin are synthesized as glycoproteins and are sulfated at various positions in vertebrates. Hyaluronan is not sulfated in vertebrates. A substantial fraction of the GlcUA residues of heparin and chondroitin are epimerized to form iduronic acid.

Many lower animals possess these same GAGs or very similar molecules. GAGs play both structural and recognition roles on the cell surface and in the extracellular matrix. By virtue of their physical characteristics, namely a high negative charge density and a multitude of polar hydroxyl groups, GAGs help hydrate and expand tissues. Numerous proteins bind selectively to one or more of the GAGs. Thus the proteins found on cell surfaces or the associated extracellular matrices (e.g. CD44, collagen, fibronectin) of different cell types may adhere or interact via a GAG intermediate. Also GAGs may sequester or bind certain proteins (e.g. growth or coagulation factors) to cell surfaces.

Certain pathogenic bacteria produce an extracellular polysaccharide coating, called a capsule, which serves as a virulence factor. In a few cases, the capsule is composed of GAG or GAG-like polymers. As the microbial polysaccharide is identical or very similar to the host GAG, the antibody response is either very limited or non-existent. The capsule is thought to assist in the evasion of host defenses such as phagocytosis and complement. Examples of this clever strategy of molecular camouflage are the production of an authentic HA polysaccharide by Gram-negative Type A *Pasteurella multocida* and Gram-positive Group A and C *Streptococcus*. The HA capsule of these microbes increases virulence by $10^2$ to $10^3$-fold as measured by $LD_{50}$ values, the number of colony forming units that will kill 50% of the test animals after bacterial challenge.

The invasiveness and pathogenicity of certain *E. coli* strains has also been attributed to their polysaccharide capsules. Two *Escherichia coli* capsular types, K4 and K5, make polymers composed of GAG-like polymers. The *E. coli* K4 polymer is an unsulfated chondroitin backbone decorated with fructose side-branches on the C3 position of the GlcUA residues. The K5 capsular material is a polysaccharide, called heparosan, identical to mammalian heparin except that the bacterial polymer is unsulfated and there is no epimerization of GlcUA to iduronic acid.

The studies of GAG biosynthesis have been instrumental in understanding polysaccharide production in general. The HA synthases were the first GAG glycosyltransferases to be identified at the molecular level. These enzymes utilize UDP-sugar nucleotide substrates to produce large polymers containing thousands of disaccharide repeats. The genes encoding bacterial, vertebrate, and viral HAS enzymes have been cloned. In all these cases, expression studies demonstrated that transformation with DNA encoding a single HAS polypeptide conferred the ability of foreign hosts to synthesize HA. Except for the most recent HAS to be identified, *P. multocida* pmHAS, these proteins have similar amino acid sequences and predicted topology in the membrane. Two classes of HASs have been proposed to exist based on these structural differences as well as potential differences in reaction mechanism.

The biochemical study of chondroitin biosynthesis in vertebrates was initiated in the 1960s. Only recently have the mammalian enzymes for elongation of the polysaccharide backbone of chondroitin been tentatively identified by biochemical means. An 80-kDa GlcUA transferase found in vertebrate cartilage and liver was implicated in the biosynthesis of the chondroitin backbone by photoaffinity labeling with an azidoUDP-GlcUA probe. A preparation from bovine serum with the appropriate GalNAc- and GlcUA-transferase activities in vitro was obtained by conventional chromatography, but several bands on SDS-polyacrylamide gels (including a few migrating ~80 kDa) were observed.

Chondroitin polysaccharide [(beta-1,3-GalNAc-beta-1,4-GlcUA)$_n$; n=~10-2000) has use as a hyaluronan (HA) polysaccharide substitute in medical or cosmetic applications. Both chondroitin and hyaluronan form viscoelastic gels (suitable for eye or joint applications) or hydrophilic, hygroscopic materials (suitable for moisturizer or wound dressings). Unmodified or underivatized chondroitin is not known to exist or, if present, in very small quantities in the human body. The main advantage is that byproducts of natural HA degradation (by shear, enzyme, radical or oxidation processes) have certain biological activities with respect to vascularization, angiogenesis, cancer, tissue modulation, but similar byproducts of chondroitin (in the proposed unsulfated, unmodified state) may not have the same biological activity. The chondroitin polymers are more inert, loosely speaking, than the analogous HA molecule. Chondroitin from either *P. multocida* Type F or a recombinant host containing the *Pasteurella*-derived or *Pasteurella*-like synthase gene will serve as an alternative biomaterial with unique properties.

With respect to related microbial GAG synthases other than the HASs, only the *E. coli* K5 glycosyltransferases, that synthesizes heparosan have been identified by genetic and biochemical means. In contrast to the HASs, it appears that two proteins, KfiA and KfiC, are required to transfer the sugars of the disaccharide repeat to the growing polymer chain. The chondroitin-backbone synthesizing enzymes of *E. coli* K4 have been enzymatically characterized, but the genes encoding the relevant glycosyltransferases have not yet been identified.

Many *P. multocida* isolates produce GAG or GAG-like molecules as assessed by enzymatic degradation and removal of the capsule of living bacterial cells. Type A *P. multocida,* the major fowl cholera pathogen, makes a capsule that is sensitive to hyaluronidase. Subsequent NMR structural studies of capsular extracts confirmed that HA was the major polysaccharide present. A specific HA-binding protein, aggrecan, also interacts with HA from Type A *P. multocida.* Two other distinct *P. multocida* types, a swine pathogen, Type D, and a minor fowl cholera pathogen, Type F, produce polymers that are chondroitin or chondroitin-like based on the observation that their capsules are degraded by *Flavobacterium* chondroitin AC lyase. After enzymatic removal of the capsule, both types were more readily phagocytosed by neutrophils in vitro. The capsule of Type D cells, but not Type F cells, is also reported to be degraded by heparinase III, suggesting a heparin-type molecule is present, too.

In the present invention, we have analyzed the monosaccharide composition of the *P. multocida* Type F polysaccharide and used the DNA sequence information of the Type A HA biosynthesis locus to obtain the homologous region from the Type F chromosome. From this research we have identified a chondroitin synthase, named pmCS (*P. multocida* Chondroitin Synthase), the first chondroitin synthase to be identified and molecularly cloned from any source. Interestingly, a single polypeptide is responsible for the copolymerization of the GlcUA and GalNAc sugars. We also identified the Type F capsular polymer as an unsulfated chondroitin polymer. We also identify organisms with the chondroitin synthase gene (Type F *P. multocida*) as new sources of unsulfated chondroitin polymer.

SUMMARY OF THE INVENTION

The present invention relates to a chondroitin synthase gene and methods of making and using same. In more particular, but not by way of limitation, the present invention relates to a chondroitin synthase gene from *Pasteurella multocida* and methods of isolating and using same. Additionally, the present invention relates to the use of unsulfated chondroitin and its preparation, as well as conversion into modified versions such as dermatan sulfate and chondroitin sulfate polymers.

BRIEF DESCRIPTION OF THE SEVERAL VIEWS OF THE DRAWINGS

FIG. 1. Sequence Alignment of pmCS and pmHAS. The two *Pasteurella* GAG synthases are highly homologous. Identical residues are denoted with the hyphen. The numbering scheme corresponds to the slightly longer pmHAS sequence. The putative A1 (residues 161-267) and A2 (residues 443-547) domains correspond to regions important for hexosamine transferase or for glucuronic acid transferase activity, respectively. Most sequence differences are found in the amino-terminal half of the polypeptides. The "consensus sequence" between pmCS and pmHAS depicts identical residues and similar residues (Consensus symbols denoted as: ! is anyone of IV; $ is anyone of LM; % is anyone of FY; # is anyone of NDQEBZ). Multalin version 5.4.1 Multiple sequence alignment with hierarchical clustering F. CORPET, 1988, Nucl. Acids Res., 16 (22), 10881-10890 Symbol comparison table: blosum62 Gap weight: 12 Gap length weight: 2 Consensus levels: high=90% low=50%

DETAILED DESCRIPTION OF THE INVENTION

Figure 2:
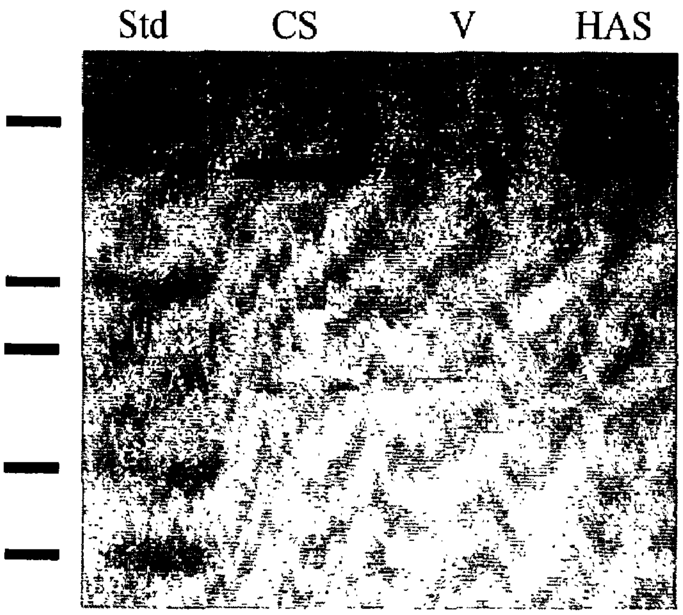
FIG. 2. Western Blot Analysis of Truncated Recombinant *PASTEURELLA* GAG Synthases. Immunoreactive bands at the predicted size of 80 kDa correspond to $pmCS^{1-704}$(CS) or $pmHAS^{1-703}$(HAS). No similar band is seen for the vector control (V). Prestained standards (Stds) are shown for size comparison.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Chondroitin Synthase ("CS") coding sequence yet is isolated away from, or purified free from, unrelated genomic DNA, for example, total *Pasteurella multocida* or, for example, mammalian host genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified pmCS (*Pasteurella multocida* Chondroitin Synthase) gene refers to a DNA segment including Chondroitin Synthase coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case pmCS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the CS gene from *Pasteurella multocida*. One such advantage is that, typically, eukaryotic enzymes may require significant post-translational modifications that can only be achieved in a eukaryotic host. This will tend to limit the applicability of any eukaryotic CS gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library and (b) the ease of manipulation because the overall size of the coding region of a prokaryotic gene is significantly smaller due to the absence of introns. Furthermore, if the product of the Chondroitin Synthase gene (i.e., the enzyme) requires posttranslational modifications or cofactors, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode a Chondroitin Synthase gene such as pmCS. In the case of pmCS, the isolated DNA segments and recombinant vectors incorporating DNA sequences which include within their amino acid sequences an amino acid sequence in accordance with SEQ ID NO: 2 or 4. Moreover, in other particular embodiments, the invention concerns isolated DNA segments and recombinant vectors incorporating DNA sequences which encode a gene that includes within its amino acid sequence the amino acid sequence of an Chondroitin Synthase gene or DNA, and in particular to an Chondroitin Synthase gene or cDNA, corresponding to *Pasteurella multocida* Chondroitin Synthase—pmCS. For example, where the DNA segment or vector encodes a full length Chondroitin Synthase protein, or is intended for use in expressing the Chondroitin Synthase protein, preferred sequences are those which are essentially as set forth in SEQ ID NO:2 or 4.

The original sequences (SEQ ID NOS: 1 and 2) differ from the corrected sequences (SEQ ID NOS: 2 and 4) because, after more extensive sequencing of the plasmid template encoding the original functional pmCS gene, we found a few mistakes made by the sequencing technician in the original DNA sequence. Basically, certain regions of the pmCS gene are very difficult to sequence accurately. Typically, one can obtain a sequence read length of 200-700 bases with a non-problematic sequence. However, in the case of pmCS gene, there were certain places where no more than 20 to 50 bases could be read, and even those were difficult. The two reasons for sequencing problems are usually due to: (1) the template, which should remain single-stranded during the reaction, forming double-stranded regions or loops in the problematic template that cause the sequencing polymerase to fall off the template prematurely, and (2) the sequencing product forms loops structures or twisted forms while running on the electrophoresis gel that do not run in the desired single-stranded conformation. We have now corrected the sequence to reflect the actual DNA and protein sequences of pmCS.

SEQ ID NO: 1 and 2 have been assigned GenBank Accession No. AF 195517.

Nucleic acid segments having chondroitin synthase activity may be isolated by the methods described herein. The term "a sequence essentially as set forth in SEQ ID NO:2 or 4" means that the sequence substantially corresponds to a portion of SEQ ID NO:2 or 4 and has relatively few amino acids which are not identical to, or a biologically functional equivalent of, the amino acids of SEQ ID NO: 2 or 4. The term "biologically functional equivalent" is well understood in the art and is further defined in detail herein, as a gene having a sequence essentially as set forth in SEQ ID NO:2 or 4, and that is associated with the ability of prokaryotes to produce chondroitin or a "chondroitin like" polymer or a chondroitin synthase polypeptide.

One of ordinary skill in the art would appreciate that a nucleic acid segment encoding enzymatically active chondroitin synthase may contain conserved or semi-conserved substitutions to the sequences set forth in SEQ ID NOS: 1, 2, 3 or 4 and yet still be within the scope of the invention.

In particular, the art is replete with examples of practitioners ability to make structural changes to a nucleic acid segment (i.e. encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019-1029 (1988) [". . . according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481-497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216-226 (1992) ["Analysis of the pattern of observed substitutions as a function of local environment shows that there are distinct patterns . . . " Compatible changes can be made.]

These references and countless others available to one of ordinary skill in the art, indicate that given a nucleic acid sequence, one of ordinary skill in the art could make substitutions and changes to the nucleic acid sequence without changing its functionality. Also, a substituted nucleic acid segment may be highly identical and retain its enzymatic activity with regard to its unadulterated parent, and yet still fail to hybridize thereto.

One of ordinary skill in the art would also appreciate that substitutions can be made to the pmCS nucleic acid segment listed in SEQ ID NO: 1 or 3 without deviating outside the scope and claims of the present invention. Standardized and accepted functionally equivalent amino acid substitutions are presented in Table I.

TABLE I

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Chared R Groups | Lysine, Arginine, Histidine |

Another preferred embodiment of the present invention is a purified nucleic acid segment that encodes a protein in accordance with SEQ ID NO:2 or 4, further defined as a recombinant vector. As used herein, the term "recombinant vector" refers to a vector that has been modified to contain a nucleic acid segment that encodes a Chondroitin Synthase protein, or fragment thereof. The recombinant vector may be further defined as an expression vector comprising a promoter operatively linked to said Chondroitin Synthase encoding nucleic acid segment.

A further preferred embodiment of the present invention is a host cell, made recombinant with a recombinant vector comprising a Chondroitin Synthase gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding Chondroitin Synthase, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

Where one desires to use a host other than *Pasteurella,* as may be used to produce recombinant chondroitin synthase, it may be advantageous to employ a prokaryotic system such as *E. coli, B. subtilis, Lactococcus* sp., or even eukaryotic systems such as yeast or Chinese hamster ovary, African green monkey kidney cells, VERO cells, or the like. Of course, where this is undertaken it will generally be desirable to bring the chondroitin synthase gene under the control of sequences which are functional in the selected alternative host. The appropriate DNA control sequences, as well as their construction and use, are generally well known in the art as discussed in more detail hereinbelow.

In preferred embodiments, the chondroitin synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which chondroitin synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the chondroitin synthase coding gene sequence together with an appropriate replication origin and under the control of selected control regions.

Thus, it will be appreciated by those of skill in the art that other means may be used to obtain the Chondroitin Synthase gene or cDNA, in light of the present disclosure. For example, polymerase chain reaction or RT-PCR produced DNA fragments may be obtained which contain full complements of genes or cDNAs from a number of sources, including other strains of *Pasteurella* or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent chondroitin synthase.

Once the DNA has been isolated it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* or *P. multocida* are employed.

Vectors such as these, exemplified by the pSA3 vector of Dao and Ferretti or the pAT19 vector of Trieu-Cuot, et al., allow one to perform clonal colony selection in an easily manipulated host such as *E. coli,* followed by subsequent transfer back into a food grade *Lactococcus* or *Bacillus* strain for production of chondroitin. These are benign and well studied organisms used in the production of certain foods and biotechnology products—otherwise known in the art as GRAS (Generally Regarded As Safe). GRAS organisms are advantageous in that one can augment the *Lactococcus* or *Bacillus* strain's ability to synthesize chondroitin through gene dosaging (i.e., providing extra copies of the HA synthase gene by amplification) and/or the inclusion of additional genes to increase the availability of the chondroitin precursors UDP-GlcUA and UDP-GalNAc. These precursors are made by the action of UDP-glucose dehydrogenase and UDP-GlcNAc/UDP-GalNAc epimerase, respectively. The inherent ability of a bacterium to synthesize chondroitin can also be augmented through the formation of extra copies, or amplification, of the plasmid that carries the chondroitin synthase gene. This amplification can account for up to a 10-fold increase in plasmid copy number and, therefore, the Chondroitin Synthase gene copy number.

Another procedure that would further augment Chondroitin Synthase gene copy number is the insertion of multiple copies of the gene into the plasmid. Another technique would include integrating the Chondroitin Synthase gene into chromosomal DNA. This extra amplification would be especially feasible, since the Chondroitin Synthase gene size is small. In some scenarios, the chromosomal DNA-ligated vector is employed to transfect the host that is selected for clonal screening purposes such as *E. coli* or *Bacillus,* through the use of a vector that is capable of expressing the inserted DNA in the chosen host. In certain instances, especially to confer stability, genes such as the chondroitin synthase gene, may be integrated into the chromosome in various positions in an operative fashion. Unlike plasmids, integrated genes do not need selection pressure for maintenance of the recombinant gene.

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable. A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO: 1, and has relatively few codons which are not identical, or functionally equivalent, to the codons of SEQ ID NO: 1. The term "functionally equivalent codon" is used herein to refer to codons that encode the same amino acid, such as the six codons for arginine or serine, as set forth in Table I, and also refers to codons that encode biologically equivalent amino acids.

It will also be understood that amino acid and nucleic acid sequences may include additional residues, such as additional N- or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and enzyme activity is concerned. The addition of terminal sequences particularly applies to nucleic acid sequences which may, for example, include various non-coding sequences flanking either of the 5' or 3' portions of the coding region or may include various internal sequences, which are known to occur within genes.

Likewise, deletion of certain portions of the polypeptide can be desirable. For example, functional truncated versions of pmHAS or pmCS missing the carboxyl terminus enhances the utility for in vitro use. (FIG. 2, Table 3) The $pmHAS^{1-703}$ and $pmCS^{1-704}$ are soluble proteins that are easy to purify in contrast to the full-length proteins (972 and 965 residues, respectively). Also, expression level increases greatly as the membrane is not overloaded. It is also contemplated that the truncated version of pmCS encompasses residues 45-704 and 75-704. These truncated versions are also highly soluble and increases expression; the native membrane proteins are found in low levels and is not soluble without special treatment with detergents.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1". Sequences which are essentially the same as those set forth in SEQ ID NO:1 may also be functionally defined as sequences which are capable of hybridizing to a nucleic acid segment containing the complement of SEQ ID NO:1 under standard or less stringent hybridizing conditions. Suitable standard hybridization conditions will be well known to those of skill in the art and are clearly set forth herein. As certain domains and active sites are formed from a relatively small portion of the total polypeptide, these regions of sequence identity or similarity may be present only in portions of the gene.

As well known in the art, most of the amino acids in a protein are present to form the "scaffolding" or general environment of the protein. The actual working parts responsible for the specific desired catalysis are usually a series of small domains or motifs. Thus a pair of enzymes that possess the same or similar motifs would be expected to possess the same or similar catalytic activity, thus be functionally equivalent. Utility for this hypothetical pair of enzymes may be considered interchangeable unless one member of the pair has a subset of distinct, useful properties. In a similar vein, certain non-critical motifs or domains may be dissected from the original, naturally occurring protein and function will not be affected; removal of non-critical residues does not perturb the important action of the remaining critical motifs or domains. By analogy, with sufficient planning and knowledge, it should be possible to translocate motifs or domains from one enzyme to another polypeptide to confer the new enzyme with desirable characteristics intrinsic to the domain or motif.

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for overnight hybridization will include 1.2-1.8×HPB at 40-50° C. or 5×SSC at 50° C. Washes in low salt (10 mM salt or 0.1×SSC) are used for stringency and room temperature incubations of 10-60 minutes.

Naturally, the present invention also encompasses DNA segments which are complementary, or essentially complementary, to the sequence set forth in SEQ ID NOS:1, 2, 3 or 4. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NOS:1, 2, 3 or 4. Recombinant vectors and isolated DNA segments may therefore variously include the Chondroitin Synthase coding regions themselves, coding regions bearing selected alterations or modifications in the basic coding region, or they may encode larger polypeptides which nevertheless include Chondroitin Synthase coding regions or may encode biologically functional equivalent proteins or peptides which have variant amino acids sequences.

The DNA segments of the present invention encompass biologically functional equivalent Chondroitin Synthase proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the Chondroitin Synthase protein or to test Chondroitin Synthase mutants in order to examine chondroitin synthase activity at the molecular level.

Also, specific changes to the Chondroitin Synthase coding sequence can result in the production of chondroitin having a modified size distribution or structural configuration. One of ordinary skill in the art would appreciate that the Chondroitin Synthase coding sequence can be manipulated in a manner to produce an altered chondroitin synthase which in turn is capable of producing chondroitin having differing polymer sizes and/or functional capabilities. For example, the Chondroitin Synthase coding sequence may be altered in such a manner that the chondroitin synthase has an altered sugar substrate specificity so that the chondroitin synthase creates a new chondroitin-like polymer incorporating a different structure via the inclusion of a previously unincorporated sugar or sugar derivative. This newly incorporated sugar could result in a modified chondroitin having different functional properties. As will be appreciated by one of ordinary skill in the art given the Chondroitin Synthase coding sequences, changes and/or substitutions can be made to the Chondroitin Synthase coding sequence such that these desired property and/or size modifications can be accomplished.

Figure 6:
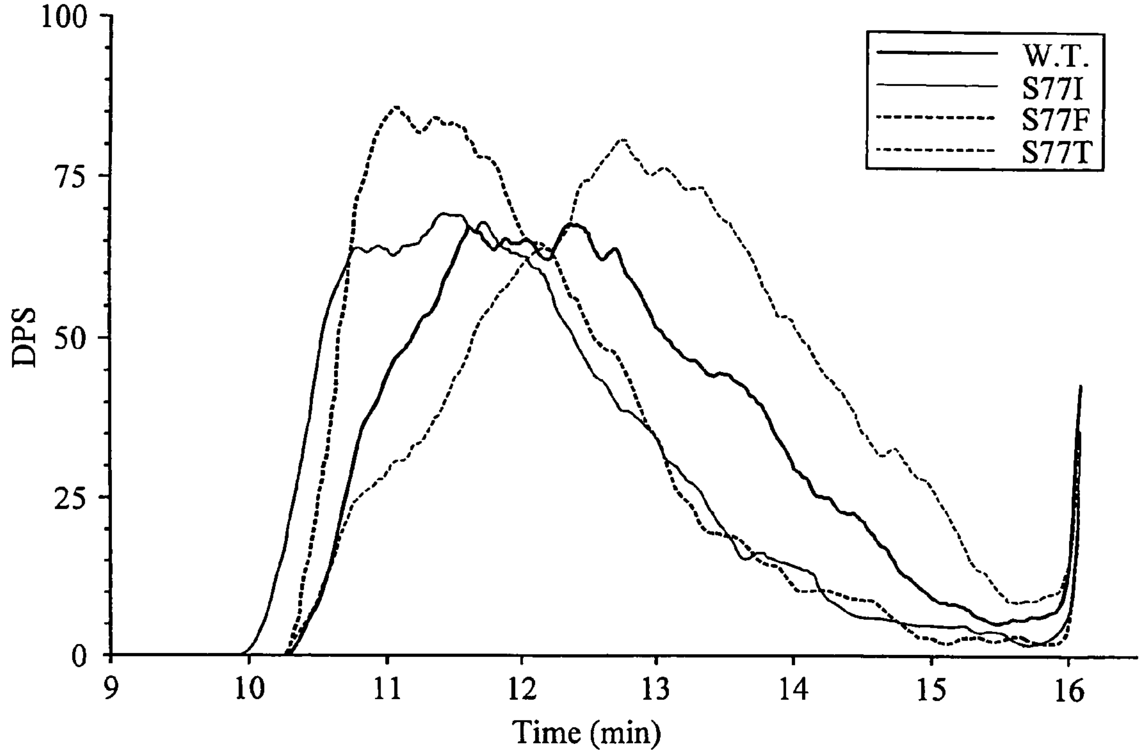
FIG. 6. HA Product Size Analysis of xIHAS1-Ser77 Mutants. The various enzymes were assayed for 5 minutes and the HA polymer products were separated by high performance gel filtration. Depending on the nature of the substituting amino acid residue at position 77, either larger or smaller HA products were formed in comparison to HA products polymerized by the wild-type enzyme. Only two mutants, Ser77Ile (larger HA) and Ser77Thr (smaller HA), and the wild-type synthase are shown. 5 min products separated on a PolySep-4000 column. For comparison, the 580-kDa dextran standard eluted at 12.5 min or 16.8 min on the 4000 or 6000 column, respectively.
Figure 7:
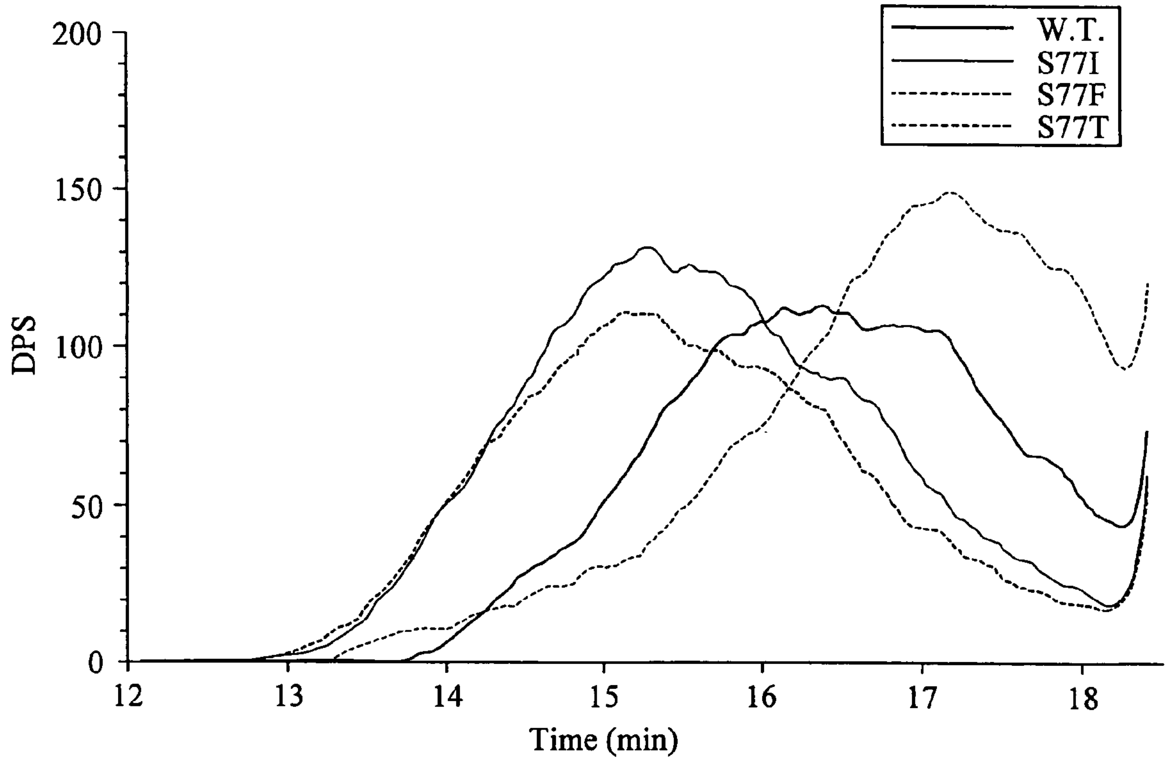
FIG. 7. HA Product Size Analysis of xIHAS1-Ser77 Mutants. The various enzymes were assayed for 30 minutes and the HA polymer products were separated by high performance gel filtration. Depending on the nature of the substituting amino acid residue at position 77, either larger or smaller HA products were formed in comparison to HA products polymerized by the wild-type enzyme. Only two mutants, Ser77Ile (larger HA) and Ser77Thr (smaller HA), and the wild-type synthase are shown. 30 min products separated on a PolySep-6000 column. For comparison, the 580-kDa dextran standard eluted at 12.5 min or 16.8 min on the 4000 or 6000 column, respectively.

Basic knowledge on the substrate binding sites (e.g. the UDP-GlcUA site or UDP-GalNAc site or oligosaccharide acceptor site) of pmCS allows the targeting of residues for mutation to change the catalytic properties of the site. The identity of important catalytic residues of pmHAS, a close homolog of pmCS, have recently been elucidated (Jing & DeAngelis, 2000, Glycobiology vol 10; pp. 883-889). Appropriate changes at or near these residues would allow other UDP-sugars to bind instead of the authentic chondroitin sugar precursors; thus a new, modified polymer is synthesized. Polymer size changes will be caused by differences in the synthase's catalytic efficiency or changes in the acceptor site affinity. Polymer size changes have been made in seHAS and spHAS (Weigel et al, Designer HA) as well as the vertebrate HAS, xIHAS1 (DG42) (Pummill & DeAngelis, unpublished data) by mutating various residues (FIGS. 6 and 7). As pmCS is a more malleable, robust enzyme than these other enzymes, similar or superior versions of mutant pmCS which synthesize modified polymers are also possible.

The term "modified structure" as used herein denotes a chondroitin polymer containing a sugar or derivative not normally found in the naturally occurring chondroitin polypeptide. The term "modified size distribution" refers to the synthesis of chondroitin molecules of a size distribution not normally found with the native enzyme; the engineered size could be much smaller or larger than normal.

Various chondroitin products of differing size have application in the areas of drug delivery and the generation of an enzyme of altered structure can be combined with a chondroitin of differing size. Applications in angiogenesis and wound healing are potentially large if chondroitin polymers of about 10-20 monosaccharides can be made in good quantities. Another particular application for small chondroitin oligosaccharides is in the stabilization of recombinant human proteins used for medical purposes. A major problem with such proteins is their clearance from the blood and a short biological half life. One present solution to this problem is to couple a small molecule shield that prevents the protein from being cleared from the circulation too rapidly. Very small molecular weight chondroitin is well suited for this role and would be nonimmunogenic and biocompatible. Larger molecular chondroitin attached to a drug or protein may be used to target the reticuloendothelial cell system which has endocytic receptors for chondroitin. Large polymers may be used in high concentrations to make gels or viscous solutions with potential for joint lubrications opthaltmic procedures, and cosmetics.

One of ordinary skill in the art given this disclosure would appreciate that there are several ways in which the size distribution of the chondroitin polymer made by the chondroitin synthase could be regulated to give different sizes. First, the kinetic control of product size can be altered by decreasing temperature, decreasing time of enzyme action and by decreasing the concentration of one or both sugar nucleotide substrates. Decreasing any or all of these variables will give lower amounts and smaller sizes of chondroitin product. The disadvantages of these approaches are that the yield of product will also be decreased and it may be difficult to achieve reproducibility from day to day or batch to batch.

Secondly, the alteration of the intrinsic ability of the enzyme to synthesize a large chondroitin product. Changes to the protein can be engineered by recombinant DNA technology, including substitution, deletion and addition of specific amino acids (or even the introduction of prosthetic groups through metabolic processing). Such changes that result in an intrinsically slower enzyme could then allow more reproducible control of chondroitin size by kinetic means. The final chondroitin size distribution is determined by certain characteristics of the enzyme that rely on particular amino acids in the sequence. Among the 10-20% of residues absolutely conserved between streptococcal hyaluronate synthase enzymes, eukaryotic hyaluronate synthase enzymes, and the pmCS, there is a set of amino acids at unique positions that may control or greatly influence the size of the polymer (either hyaluronan or chondroitin) that the enzyme can make.

As shown in FIGS. 6 and 7, HA Product Size Analysis of xIHAS 1-Ser77 Mutants. The various enzymes were assayed for 5 or 30 minutes and the HA polymer products were separated by high performance gel filtration. Depending on the nature of the substituting amino acid residue at position 77, either larger or smaller HA products were formed in comparison to HA products polymerized by the wild-type enzyme. Only two mutants, Ser77Ile (larger HA) and Ser77Thr (smaller HA), and the wild-type synthase are shown. Panel A: 5 min products separated on a PolySep-4000 column. Panel B: 30 min products separated on a PolySep-6000 column. For comparison, the 580-kDa dextran standard eluted at 12.5 min or 16.8 min on the 4000 or 6000 column, respectively.

Specific changes in any of these residues can produce a modified hyaluronan or chondroitin that produces a hyaluronan or chondroitin product having a modified size distribution. Engineered changes to seHAS, spHAS, pmHAS, cvHAS, pmCS that decrease the intrinsic size of the hyaluronan or chondroitin polymer that the enzyme can make before the hyaluronan or chondroitin is released, will provide powerful means to produce either a hyaluronan or chondroitin polymer product of smaller or potentially larger size than the native enzyme.

Finally, larger molecular weight chondroitin made be degraded with specific chondroitinidases to make lower molecular weight chondroitin. This practice, however, is very difficult to achieve reproducibility and one must meticulously repurify the chondroitin to remove the chondroitinidases and unwanted digestion products.

Structurally modified chondroitin is no different conceptually than altering the size distribution of the chondroitin product by changing particular amino acids in the desired Chondroitin Synthase and/or more particularly, but not limiting thereto pmCS. Derivatives of UDP-GalNAc, in which the acetyl group is missing from the amide (UDP-GalN) or replaced with another chemically useful group (for example, phenyl to produce UDP-GalNPhe), are expected to be particularly useful. The free amino group would be available for chemical reactions to derivatize chondroitin in the former case with GalN incorporation. In the latter case, GalNPhe, would make the polymer more hydrophobic or prone to making emulsions. The strong substrate specificity may rely on a particular subset of amino acids among the 10-20% that are conserved. Specific changes to one or more of these residues creates a functional chondroitin synthase that interacts less specifically with one or more of the substrates than the native enzyme. This altered enzyme could then utilize alternate natural or special sugar nucleotides to incorporate sugar derivatives designed to allow different chemistries to be employed for the following purposes: (i) covalently coupling specific drugs, proteins, or toxins to the structurally modified chondroitin for general or targeted drug delivery, radiological procedures, etc. (ii) covalently cross linking the hyaluronic acid itself or to other supports to achieve a gel, or other three dimensional biomaterial with stronger physical properties, and (iii) covalently linking hyaluronic acid to a surface to create a biocompatible film or monolayer.

EXPERIMENTAL PROCEDURES

Materials and *Pasteurella* Strains—Unless otherwise noted, all chemicals were from Sigma or Fisher, and all molecular biology reagents were from Promega. The wild-type encapsulated Type F *P. multocida* strains, P-4679 and P-3695, were obtained from Dr. Richard Rimler (USDA, Ames, Iowa). These strains were isolated from turkeys with fowl cholera. P-4679 had a slightly larger capsule than P-3695 as judged by light microscopy and India Ink staining. The latter strain also possessed an endogenous uncharacterized plasmid.

Carbohydrate Analysis of Type F Capsular Material—The anionic polymer in the capsule of Type F bacteria was purified by urea extraction and cetylpyridinium chloride precipitation. P-4679 was grown in complete defined media (150 ml) with mild shaking overnight at 37° C. Cells were harvested by centrifugation (3,000×g, 10 min) and washed twice with 0.1 M NaCl by repeated centrifugation and resuspension. The capsule was removed by extraction with 3 ml of 8 M urea for 8 min at 98° C. The cells were removed by high-speed centrifugation (15,000×g, 10 min) and the urea solution was extracted with one volume of chloroform thrice at 22° C. GAGs in the aqueous extract were precipitated by the addition of cetylpyridinium chloride (1% w/v final concentration). Substantial polysaccharide may also be precipitated from the spent culture media in a similar fashion. After standing for 10 min, the precipitate was collected by high-speed centrifugation and redissolved in 2.5 M NaCl. The mixture was clarified by high-speed centrifugation and the supernatant was precipitated with 3 vol of ethanol. The precipitate was washed with 70% ethanol, dried slightly, and resuspended in 2.5 M NaCl. The ethanol precipitation procedure was repeated and the pellet was redissolved in water. Another round of ethanol precipitation (2 vol) was performed. The final GAG pellet was dissolved in water. The yield (0.6 mg uronic acid from all extract) was determined with the carbazole assay for uronic acid using a glucuronolactone standard.

The monosaccharide composition of the GAG extract was determined by acid hydrolysis (2 M HCl, 4 hrs, 100° C.) and high pH anion exchange chromatography. The hydrolyzate was repeatedly diluted in water and dried under vacuum to remove HCl, then mixed with a rhamnose standard, and clarified using a 0.2 μm spin filter. Portions of the hydrolyzate (about 5 nmoles of uronic acid) were injected onto a PA-I column (Dionex) equilibrated with 12 mM NaOH. After isocratic elution (25 min) to separate the neutral sugars, a gradient of sodium acetate (0 to 0.18 M in 30 min) was utilized to separate the acidic sugars. Eluted compounds were detected by pulsed amperometric detection. In parallel runs, the Type F sample was spiked with known monosaccharide standards of authentic chondroitin sulfate C (derived from shark cartilage) hydrolyzate. HA and heparin hydrolyzate standards were also run. Retention times relative to the rhamnose internal standard were calculated.

PCR Analysis of Type F Genomic DNA—Preliminary data from Southern blot analysis using pmHAS hybridization probes suggested that the Type A and the Type F microbes were very homologous at the capsule locus. PCR was utilized to verify these findings. Type F chromosomal DNA (0.1 μg) served as a template in PCR reactions (20 μl) utilizing oligonucleotide primers corresponding to various regions of the Type A capsule locus genes. After 40 cycles of PCR (94° C. 30 5; 42° C. 30 5; 72° C. 4 min) with Taq DNA polymerase in the supplied buffer (Fisher), the samples were separated by agarose gel electrophoresis. Many primer pairs, but not all, amplified Type F DNA to yield products of the predicted size assuming that Type A and Type F loci were homologous. Two primers (Pm10, 5'-CACTGTCTAACTTTATTGTTAGCC-3' SEQ ID NO: 5; Pm21,5'-TTTTTAACGAATAGGCTGTC-3' SEQ ID NO: 6) were chosen to amplify a 3.6 kb portion of the Type F locus predicted to contain the DNA encoding carboxyl-terminal half of the KfaA homolog and the amino-terminal portion of the putative polysaccharide synthase. The product from a PCR reaction (26 cycles) was cloned into a TA vector (Invitrogen) according to the manufacturer guidelines. The plasmid was analyzed by cycle sequencing (ThermoSequenase® system with $^{33}$P-terminators, Amersham) with the Pm10 or the Pm21 primer. The preliminary sequence data from the PCR product derived from Type F DNA was highly (about 80%) homologous to the sequence of the Type A locus. Therefore, the 3.6-kb insert was excised from the plasmid, gel-purified, and labeled with digoxigenin (High Prime system, Boehringer Mannheim) to serve as a hybridization probe.

Isolation of Capsule Biosynthesis Locus DNA—A lambda library of Sau3A partially digested P-4679 DNA (4-9 kb average length insert) was made using the BamHI-cleaved) Zap Express™ vector system (Stratagene). The plaque lifts were screened by hybridization (5×SSC, 50° C.; 16 hrs) with the digoxigenin-labeled probe using the manufacturer guidelines for colorimetric development. *E. coli* XLI-Blue MRF' was co-infected with the purified, individual positive lambda clones and ExAssist helper phage to yield phagemids. The resulting phagemids were transfected into *E. coli* XLOLR cells to recover the plasmids. Sequence analysis of the plasmids revealed a novel open reading frame, i.e. pmCS, with high homology to pmHAS (87%).

Expression of Recombinant *P. multocida* Chondroitin Synthase—In previous studies with pmHAS, a functional, soluble enzyme was created if a portion of the carboxyl terminus was truncated by molecular genetic means. Therefore, a portion of the pmCS ORF (residues 1-704) in the insert of one of the excised lambda clones, pPmF4A, was amplified by 20 cycles of PCR with Taq polymerase. The sense primer corresponded to the sequence at the deduced amino terminus of the ORF and the antisense primer encoded the new carboxyl terminus followed by an artificial stop codon. The resulting PCR product was purified and concentrated using GeneClean. This insert was cloned using the pETBlue-1 Acceptor system (Novagen) according to the manufacturer's instructions. The Taq-generated single A overhang is used to facilitate the cloning of the open reading frame downstream of the T7 promoter and the ribosome binding site of the vector. The ligated products were transformed into *E. coli* NovaBlue and plated on LB carbenicillin (50 μg/ml) and tetracycline (15 μg/ml) under conditions for blue/white screening.

White or light blue colonies were analyzed by restriction digestion. A clone containing a plasmid with the desired truncated ORF, pPm-CS$^{1-704}$, was transformed into *E. coli* Tuner, the T7 RNA polymerase-containing expression host, and maintained on LB media with carbenicillin and chloramphenicol (34 μg/ml) at 30° C. Log phase cultures were induced with 13-isopropylthiogalactoside (0.2 mM final) for 5 hrs. The cells were harvested by centrifugation, frozen, and extracted for 20 mm with a mild detergent (bPer II reagent, Pierce) at 7° C. in the presence of a broad-range protease inhibitor cocktail. The cells were removed by centrifugation and the soluble extract was used as the source of Chondroitin Synthase enzyme for in vitro assays.

Western Blot Analysis of Recombinant *P. multocida* Chondroitin Synthase—A monospecific polyclonal antibody was generated against a synthetic peptide (acetyl-LDSDDYLEPDAVELCLKEF-amide SEQ ID NO: 7) corresponding to residues 526 to 544 of the pmHAS protein. The bPer extracts of various recombinant *E. coli* strains were heated at 42° C. for 10 mm in sample buffer before loading. After electrophoresis, semi-dry transfer to a nitrocellulose membrane was performed. The Western blots were blocked with bovine serum albumin and incubated with the affinity-purified antibody before detection with a Protein A-alkaline phosphatase conjugate and calorimetric development with bromochloroindolyl phosphate and nitro blue tetrazolium.

Assays for Chondroitin Synthase Activity—Incorporation of radiolabeled monosaccharides from UDP-[$^{14}$C]GlcUA and/or UDP-[$^{3}$H]GalNAc precursors (NEN) was used to monitor chondroitin synthase activity. Samples were usually assayed in a buffer containing 50 mM Tris, pH 7.2, 20 mM $MnCl_2$, 0.1 M $(NH_4)_2SO_4$, 1 M ethylene glycol, 0-0.6 mM UDP-GlcUA, and 0-0.6 mM UDP-GalNAc in the presence of a chondroitin-6-sulfate acceptor oligosaccharide, [GalNAc-6-$SO_4$GlcUA-GalNAc-6-$SO_4$]n (n=1 or 2; gift of Dr. Geetha Sugumaran), at 30° C. The reaction products were separated from substrates by descending paper (Whatman 3M) chromatography with ethanol/1M ammonium acetate, pH 5.5, development solvent (65:35). The origin of the paper strip was cut out, eluted with water, and the incorporation of radioactive sugars into HA polymer was detected by liquid scintillation counting with BioSafe II cocktail (RPI). To test the transfer specificity of pmCS$^{1-704}$ various UDP-sugars (UDP-GlcNAc, UDP-GalUA, UDP-Glc) were substituted for the authentic chondroitin precursors.

Size Analysis and Enzymatic Degradation of Labeled Polymers—Gel filtration chromatography was used to analyze the size distribution of the labeled polymers. Separations were performed with a Polysep-GFC-P 5000 column (300×7.8 mm; Phenomenex) eluted with 0.2 M sodium nitrate at 0.6 ml/min. Radioactivity was monitored with an in-line Radioflow LB508 detector (EG & G Berthold) using Unisafe I cocktail (1.8 ml/min; Zinsser). The column was standardized with fluorescein-labeled dextrans of various sizes. To identify the radiolabeled polymers, portions of some reactions were dialyzed into water (3 kDa cutoff) and the high molecular weight product was digested with various glycolytic enzymes for 7 hours at 37° C. The enzyme concentrations and digestion buffers were: *Flavobacterium* chondroitin AC lyase, 1 milliunit/μl, 50 mM Tris-acetate, pH 7.5; Proteus chondroitin AC lyase, 1 milliunit/μl, 50 mM Tris-acetate, pH 8; *Streptomyces* HA lyase, 266 milliunits/μl, 50 mM sodium acetate, pH 5.4.

If cells without formidable cell membrane barriers are used as host cells, transfection is carried out by the calcium phosphate precipitation method, well known to those of skill in the art. However, other methods may also be used for introducing DNA into cells such as by nuclear injection, cationic lipids, electroporation, protoplast fusion or by the Biolistic(tm) Bioparticle delivery system developed by DuPont (1989). The advantage of using the DuPont system is a high transformation efficiency. If prokaryotic cells or cells which contain substantial cell wall constructions are used, the preferred method of transfection is calcium treatment using calcium chloride to induce competence or electroporation.

Construction of suitable vectors containing the desired coding and control sequences employ standard ligation techniques. Isolated plasmids or DNA fragments are cleaved, tailored, and religated in the form desired to construct the plasmids required. Cleavage is performed by treating with restriction enzyme (or enzymes) in suitable buffer. In general, about 1 μg plasmid or DNA fragments are used with about 1 unit of enzyme in about 20 μl of buffer solution. Appropriate buffers and substrate amounts for particular restriction enzymes are specified by the manufacturer. Incubation times of about 1 hour at 37° C. are workable.

After incubations, protein is removed by extraction with phenol and chloroform, and the nucleic acid is recovered from the aqueous fraction by precipitation with ethanol. If blunt ends are required, the preparation is treated for 15 minutes at 15° C. with 10 units of Polymerase I (Klenow), phenol-chloroform extracted, and ethanol precipitated. For ligation approximately equimolar amounts of the desired components, suitably end tailored to provide correct matching are treated with about 10 units T4 DNA ligase per 0.5 μg DNA. When cleaved vectors are used as components, it may be useful to prevent religation of the cleaved vector by pretreatment with bacterial alkaline phosphatase.

For analysis to confirm functional sequences in plasmids constructed, the first step was to amplify the plasmid DNA by cloning into specifically competent *E. coli* SURE cells (Stratagene) by doing transformation at 30-32° C. Second, the recombinant plasmid is used to transform *E. coli* K5 strain Bi8337-41, which can produce the UDP-GlcA precursor, and successful transformants selected by antibiotic resistance as appropriate. Plasmids from the library of transformants are then screened for bacterial colonies that exhibit HA production. These colonies are picked, amplified and the plasmids purified and analyzed by restriction mapping. The plasmids showing indications of a functional Chondroitin Synthase gene are then further characterized by any number of sequence analysis techniques which are known by those of ordinary skill in the art.

In general, prokaryotes are used for the initial cloning of DNA sequences and construction of the vectors useful in the invention. It is believed that a suitable source may be bacterial cells, particularly those derived from strains that can exist on a simple minimal media for ease of purification. Bacteria with a single membrane, but a thick cell wall such as *Staphylococci* and *Streptococci* are Gram-positive. Gram-negative bacteria such as *E. coli* contain two discrete membranes rather than one surrounding the cell. Gram-negative organisms tend to have thinner cell walls. The single membrane of the Gram-positive organisms is analogous to the inner plasma membrane of Gram-negative bacteria. Additionally, many bacteria possess transport systems that help capsular polymers be secreted from the cell.

For the expression of Chondroitin Synthase in a form most likely to accommodate Chondroitin Synthase synthesis, one may desire to employ *Streptococcus* species such as *S. equisimilis* or *S. zooepidemicus* and/or P. *multocida* and/or *Bacillus* Strains. The aforementioned strains, as well as *E. coli* W3110 (F-, lambda-, prototrophic, ATCC No. 273325), bacilli such as Bacillus subtilis, or other enterobacteriaceae such as *Serratia marcescens,* could be utilized to generate a "super" Chondroitin Synthase containing host.

In general, plasmid vectors containing origins of replication and control sequences which are derived from species compatible with the host cell are used in connection with these hosts. The vector ordinarily carries an origin of replication, as well as marking sequences which are capable of providing phenotypic selection in transformed cells. For example, *E. coli* is typically transformed using pBR322, a plasmid derived from an *E. coli* species. pBR322 contains genes for ampicillin and tetracycline resistance and thus provides easy means for identifying transformed cells. A pBR plasmid or a pUC plasmid, or other microbial plasmid or phage must also contain, or be modified to contain, promoters which can be used by the microbial organism for expression of its own proteins.

Those promoters most commonly used in recombinant DNA construction include the lacZ promoter, tac promoter, the T7 bacteriophage promoter, and tryptophan (trp) promoter system. While these are the most commonly used, other microbial promoters have been discovered and utilized, and details concerning their nucleotide sequences have been published, enabling a skilled worker to ligate them functionally with plasmid vectors. Also for use with the present invention one may utilize integration vectors.

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in *Saccharomyces,* the plasmid YRp7, for example, is commonly used. This plasmid already contains the trp1 gene which provides a selection marker for a mutant strain of yeast lacking the ability to grow without tryptophan, for example, ATCC No. 44076 or PEP4-1. The presence of the trp1 lesion as a characteristic of the yeast host cell genome then provides an effective environment for detecting transformation by growth in the absence of tryptophan. Suitable promoting sequences in yeast vectors include the promoters for the galactose utilization genes, the 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, cytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture has become a routine procedure in recent years. Examples of such useful host cell lines are VERO and HeLa cells, Chinese hamster ovary (CHO) cell lines, and WI38, BHK, COS, and MDCK cell lines.

For use in mammalian cells, the control functions on the expression vectors are often provided by viral material. For example, commonly used promoters are derived from polyoma, Adenovirus 2, bovine papilloma virus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg1 I site located in the viral origin of replication.

Further, it is also possible, and often desirable, to utilize promoter or control sequences normally associated with the desired gene sequence, provided such control sequences are compatible with the host cell systems. An origin of replication may be provided either by construction of the vector to include an exogenous origin, such as may be derived from SV40 or other viral (e.g., Polyoma, Adeno, BPV) source, or may be provided by the host cell chromosomal replication mechanism. If the vector is integrated into the host cell chromosome, the latter mechanism is often sufficient.

Chondroitin sulfate and dermatan sulfate are both derived from the same polymer, i.e. D-glucuronic acid beta (1-3)D-N-acetyl galactosamine beta (1-4). Both chondroitin sulfate and dermatan sulfate can be sulfated at positions 4 or 6 of N-acetyl galactosamine and position 2 of the uronic acid. Neither has been observed to be N-sulfated in nature. The difference between chondroitin sulfate and dermatan sulfate is the epimerisation of glucuronic acid to iduronic acid. There are problems however with the nomenclature and designation of a polysaccharide as either chondroitin sulfate or dermatan sulfate. In particular, the frequency with which iduronic acid must occur rather than glucuronic acid, for the chain to be called a dermatan sulfate chain, is open to interpretation. Thus a chondroitin sulfate chain may have sequences of dermatan sulfate interspersed therein and visa versa. One of ordinary skill in the art would appreciate, however, that a polymer having between 10% and 50% epimerisation of glucuronic acid to iduronic acid would be suitably designated a dermatan sulfate polysaccharide.

A chondroitin polymer is produced by a chondroitin synthase and in particular, but not limited thereto, the pmCS of the present invention. For example, the chondroitin polymer can be converted into a dermatan molecule that may be an even more valuable product than chondroitin itself. The chondroitin polymer can be converted into dermatan either in the purified form or in vivo (i.e. in the host itself). For example, Chang et al. have identified and detailed a reaction of *Azotobacter vinelandii* poly-beta-D-mannuronic acid C-5-epimerase on synthetic D-glucuronans. A dermatan molecule can be made using the *Azotobacter vinelandii* poly-beta-( 1->4)-D-mannuronic acid C-5-epimerase to react with a chondroitin polymer made via a chondroitin synthase such as pmCS. (Chang et al. *Action of Azotobacter vinelandii poly-beta-D-mannuronic Acid C-5-epimerase on Synthetic D-Glucuronans,* Carbohydrate Research, Dec. 1, 2000; 329(4):913-22, which is expressly incorporated herein in its entirety by reference). U.S. Pat. No. 5,939,289 issued to Ertesvag et al., which is expressly incorporated herein by reference, also discloses a C-5 epimerase which may be used to convert the chondroitin molecule produced by the *P. multocida* chondroitin synthase into a unsulfated dermatan molecule. The c-5 epimerase is expected to work on the chondroitin polymer as the Chang et al. paper describes epimerization of a variety of polysaccharides containing uronic acids including oxidized starch and chitin.

Alternatively, instead of step-wise chondroitin synthesis followed by epimerization reaction, an in vivo combined method should be possible. This is very suitable in pmCS/*Azotobacter epimerase* case as the reactions are compatible and both genes are from Gram-negative bacteria. Both enzymes have been shown to function in *E. coli.* Placing both genes in one cell and allowing contact of chondroitin and the epimerase results in the desired product.

Further, an assay procedure for measuring the reactions catalyzed by polyuronic acid C-5 epimerases can be used. (See e.g., Chang et al. *Measurement of the Activity of Polyuronic Acid C-*5 *Epimerases,* Anal. Biochem., Apr. 10, 1998; 258(1):59-62, which is expressly incorporated herein in its entirety by reference) Action of C-5 epimerases inverts the C-6 carboxyl group of polyuronic acids thus converting beta-linked residues into alpha-linked residues or vice versa. The above-identified assay takes advantage of the greater susceptibility of the acid hydrolysis of alpha-glycosidic linkages than beta-glycosidic linkages. Thus, acid treatment of experimental polymers (the product) results in a color yield but the parent starting material does not result in a substantial color yield. The method of this particular assay involves the partial acid hydrolysis of the polyuronic acid before and after reaction with the C-5 epimerase. The greater or lesser amounts of uronic acid released (solubilized) before and after reaction of the C-5 epimerase are a measure of the amount of alpha- or beta-glycosidic linkages that are formed and a measure of the amount of catalysis by the enzyme. In this manner, the conversion chondroitin polymer to dermatan can be catalyzed and monitored for reaction and efficiency.

The chondroitin molecule made by the pmCS enzyme is an ideal polymeric starting material for the creation of a dermatan sulfate molecule. Certain mammalian epimerases only epimerize unsulfated polymer molecules. For example, the C-5 uronosyl epimerase, which is capable of converting a chondroitin molecule into a dermatan molecule, will only epimerize an unsulfated chondroitin molecule. Unsulfated chondroitin molecules are not found in nature, and chondroitin sulfate must be either desulfated or an unsulfated chondroitin molecule must be recombinantly produced. Since no chondroitin synthase has been known prior to or since the discovery of the pmCS enzyme, one of ordinary skill in the art would have to expend additional time, money, and capital in order to convert sulfated chondroitin into unsulfated or desulfated chondroitin. Once the chondroitin is unsulfated, the mammalian epimerases can be used to convert the chondroitin molecule into a dermatan molecule. By utilizing a chondroitin synthase, such as pmCS, one of ordinary skill in the art is capable of producing an unsulfated chondroitin molecule which is an ideal starting material for epimerization by a mammalian epimerase. For one such mammalian epimerase and methods of using same, see e.g. Malmstrom A., *Biosynthesis of Dermatan Sulfate—Substrate Specificity of the C-*5 *Uronosyl Epimerase,* J. Biol. Chem., Jan. 10, 1984; 259(1): 161-5, which is expressly incorporated herein by reference in its entirety.

Utilizing enzymatic sulfation, the chondroitin polymer—turned—dermatan molecule can be sulfated, thereby creating an even more valuable and flexible polymer for anticoagulation, device coatings, and/or other biomaterial. As pointed out in the Eklund et al. article entitled *Dermatan is a Better Substrate for* 4-*O-sulfation than Chondroitin: Implications in the Generation of* 4-*O-sulfated. L-iduronic-rich Galactosaminoglycans,* Arch. Biochem. Biophys., Nov. 15, 2000; 383(2):171-7, which is expressly incorporated in its entirety herein by reference, dermatan is not only more easily enzymatically sulfated than chondroitin, but sulfated dermatan is a more valuable, flexible and useful product than chondroitin. Thus, utilizing a chondroitin synthase such as pmCS, one or ordinary skill in the art, given the present disclosure, would be able to produce natural and non-natural chondroitin as well as dermatan and dermatan sulfate. Other articles, which are expressly incorporated herein in their entirety by reference, outline other methodologies for enzymatically sulfating dermatan. Bhakta et al. *Sulfation of N-acetylglucosamine by Chondroitin* 6-*Sulfotransferase* 2 (*GST*-5), J. Biol. Chem., Dec. 22, 2000; 275(51):40226-34; Ito et al. *Purification and Characterization of N-acetylgalactosamine* 4-*sulfate* 6-*O-Sulfotransferase from the Squid Cartilage,* J. Biol. Chem., Nov. 3, 2000; 275(44):34728-36.

In addition to enzymatic sulfation, the dermatan polymer can be chemically sulfated. One method for chemical sulfation is outlined in the article by Garg et al. entitled *Effect of Fully Sulfated Glycosaminoglycans on Pulmonary Artery Smooth Muscle Cell Proliferation,* Arch. Biochem. Biophys., Nov. 15,1999; 371(2): 228-33, which is expressly incorporated herein in its entirety by reference. Typically, the polysaccharide in an anhydrous solvent is treated with sulfur trioxide or chlorosulfonic acid. In any event, one of ordinary skill in the art given the chondroitin synthase (pmCS) of the present invention and the methodology for producing a chondroitin polymer from the pmCS enzyme, would be capable of using the epimerization reaction to form a dermatan molecule and then sulfating this dermatan molecule by known enzymatic, or chemical sulfation techniques. Alternatively, unepimerimized chondroitin could be sulfated by any means as well.

Also, U.S. Pat. No. 4,990,601 issued to Skjak-Braek et al., which is expressly incorporated herein by reference in its entirety, discloses a chemical process using supercritical $CO_2$ which epimerizes uronic acid in a compound. Utilizing a chondroitin polypeptide using the pmCS of the present invention and the $CO_2$ epimerization method of Skjak-Braek et al., one of ordinary skill in the art can easily make unsulfated dermatan molecules.

Figure 5:
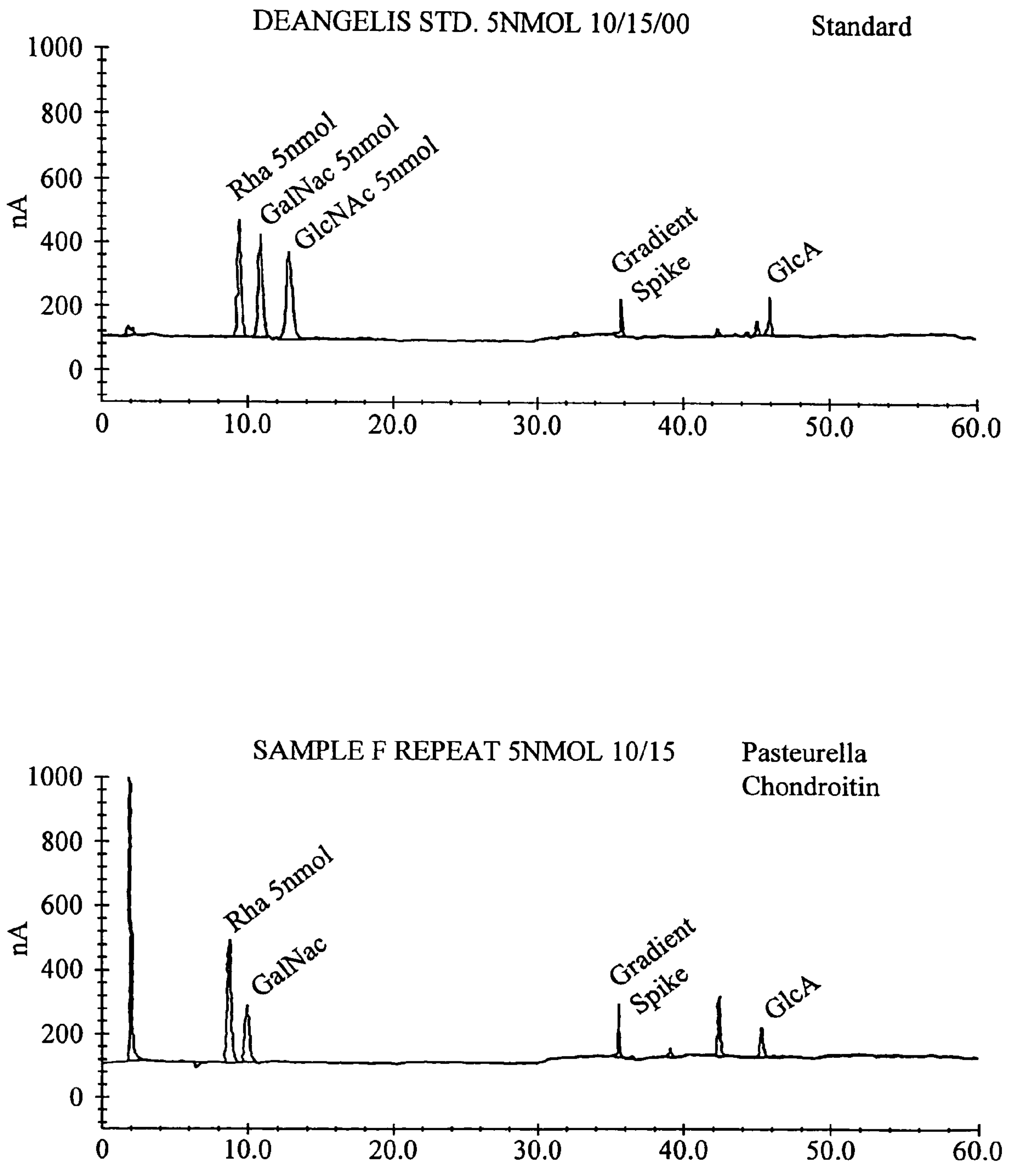
FIG. 5. Monosaccharide Analysis of Type F Polymer. The examples of the actual chromatogram used to generate the sugar composition data in Table 2 are shown here. The profiles graph the amperometric response (y-axis signifying the relative amount of sugar eluting from column; units nA=nanoamperes) versus elution time (x-axis signifying the distinct monosaccharides; units=minutes). All injected samples (containing about 5 nanomoles of each sugar component) were spiked with an internal standard, rhamnose (Rha), to assess recovery and the column performance. The "DeAngelis Standard" contains a mixture of GalNAc, GlcNAc, and GlcUA that were subjected to hydrolysis. The "Sample F" is a hydrolysate of Type F polymer. The analysis shows that the Type F polymer is composed of only GalN (hydrolysis removes the acetyl group converting GalNAc into GalN) and GlcUA monosaccharides.

Compositional Analysis of Type F *P. multocida* Polymer—Previous work by others had shown that the Type F capsule is removed from bacterial cells by treatment with chondroitin AC lyase. We found that a fragment of the specific HA-binding protein, aggrecan, in the HA-TEST assay (Pharmacia) did not cross-react with extracts of the Type F polymer, but readily detected the HA in parallel extracts from Type A bacteria. Acid hydrolysis and monosaccharide analysis of the Type F polymer showed that it contained the sugars galactosamine and GlcUA (Table 2 and FIG. 5).

TABLE 2

Monosaccharide Composition of Type F Polymer and Various GAGs. Acid hydrolysis and high pH ion exchange chromatography were utilized to determine the sugar components of the Type F polymer (F). The polysaccharides chondroitin sulfate C (C), hyaluronan (HA), and heparin (HEP), and pure monosaccharides were used as standards. Under these hydrolysis conditions, deacetylation and desulfation as well as the desired fragmentation of glycosidic bonds occur. Retention times relative to the internal standard rhamnose elution time (10.7 min; set to 1) are presented for the relevant hexosamines. Acidic sugars were eluted with a sodium acetate gradient; the retention time of the major uronic acid peak from the start of the gradiant is presented. Type F polysaccharide and chondroitin sulfate possess the identical monsaccharide composition, galactosamine and glucuronic acid.

| | Polysaccharides | | | | |
|---|---|---|---|---|---|
| Sugar | C | C/F MIX | F | HA | HEP |
| | Retention Time Relative to Rhamnose | | | | |
| glucosamine | ND* | ND | ND | 1.38 | 1.38 |
| galactosamine | 1.14 | 1.12 | 1.12 | ND | ND |
| | Retention time (min) | | | | |
| uronic acid | 14.87 | 14.87 | 14.87 | 14.85 | 14.58 |

*ND, not detected

Figure 8:
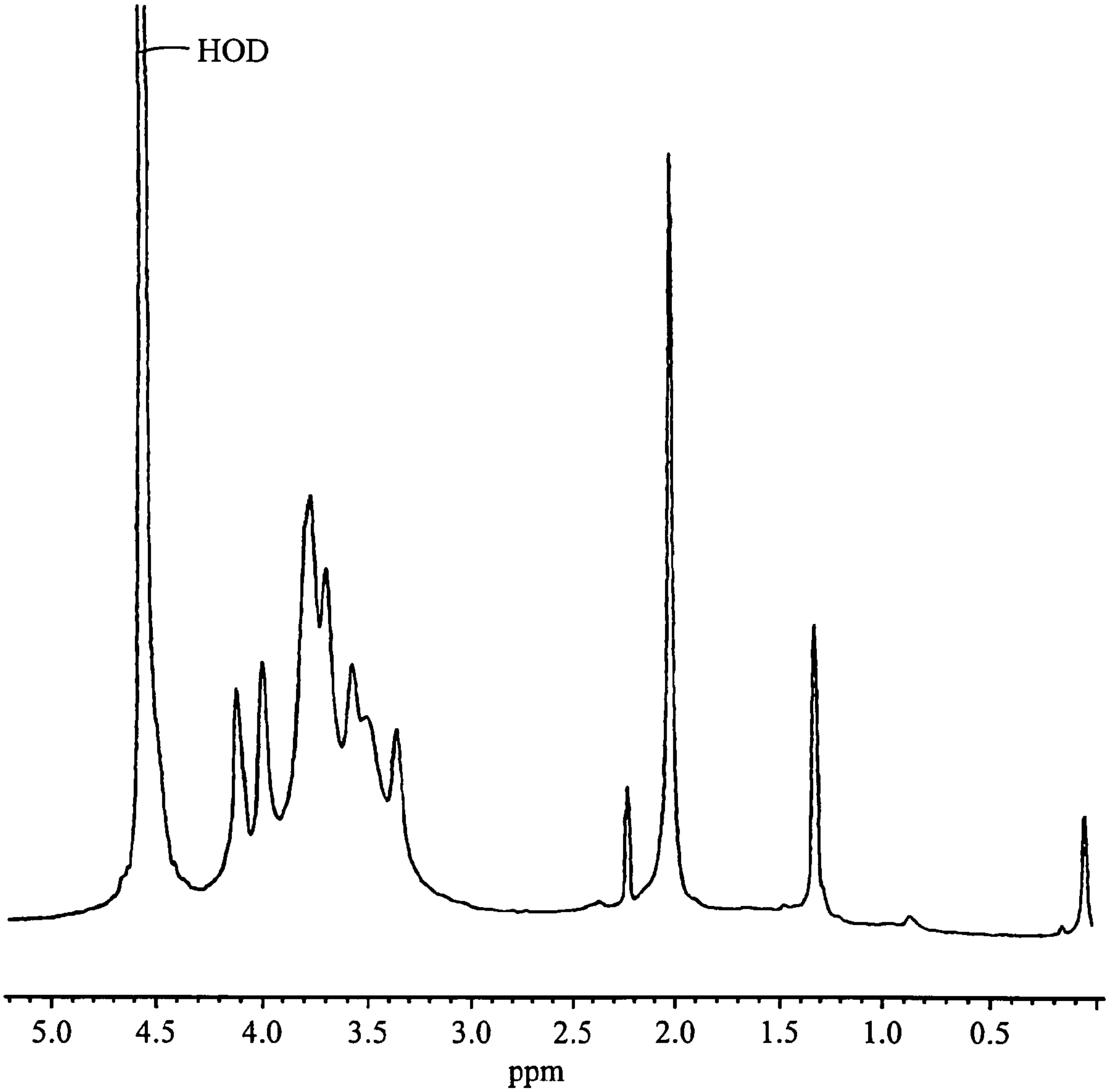
FIG. 8. NMR Analysis—Type F polysaccharide (170 ug uronic acid based on carbazole reaction) was exchanged into deuterated water ($D_2O$) and the proton spectrum (H-NMR) was acquired at 45° C. at 500 MHz. The chemical shifts (ppm) of the peaks are consistent with an unsulfated chondroitin polymer.
Figure 9:
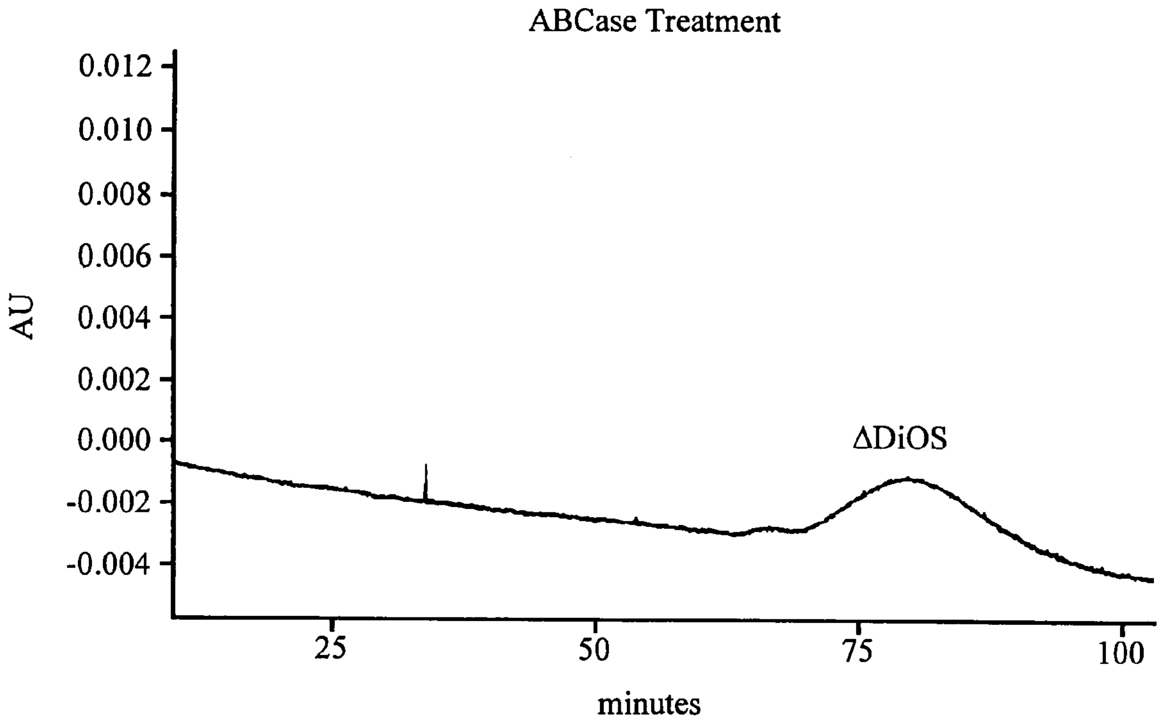
FIG. 9. Disaccharide Composition Analysis—Samples were dissolved in 10 μl of 50 mM Tris-HCl and 60 mM sodium acetate buffer, pH 8, and 20 mU Chondroitinase ABC was added separately. The digestions were kept in a 37° C. water bath overnight. The enzymes were deactivated by boiling for 2 min. The experiments were performed with a capillary electrophoresis P/ACE 5500 System (Beckman Instruments, Fullerton, Calif.) at a constant capillary temperature of 18° C. with a potential of −22 kV by UV absorbance at 232 nm. The electropherograms were acquired using the system Gold software package (Beckman Instruments, Fullerton, Calif.). Separation and analysis were carried out in a reversed polarity mode using a fused silica (externally coated except where the tube passed through the detector) capillary tube (50 μm inner diameter, 360 μm outer diameter, 57 cm long, and 49 cm effective length). Prior to every run, the capillary was conditioned with 0.5M NaOH (1 min, 20 psi) and rinsed (1 min, 20 psi) with separation buffer (20 mM $H_3PO_4$ adjusted to pH 3.5 with saturated dibasic sodium phosphate). Samples were applied by pressure injection 25 s at 0.5 psi. Standards of all potential chondroitin oligosaccharides were used to calibrate the capillary. The unsulfated disaccharide, ΔDiOS, was observed in digests of Type F polymer. Thus, the native polymer of Type F is an unsulfated chondroitin.
Figure 10:
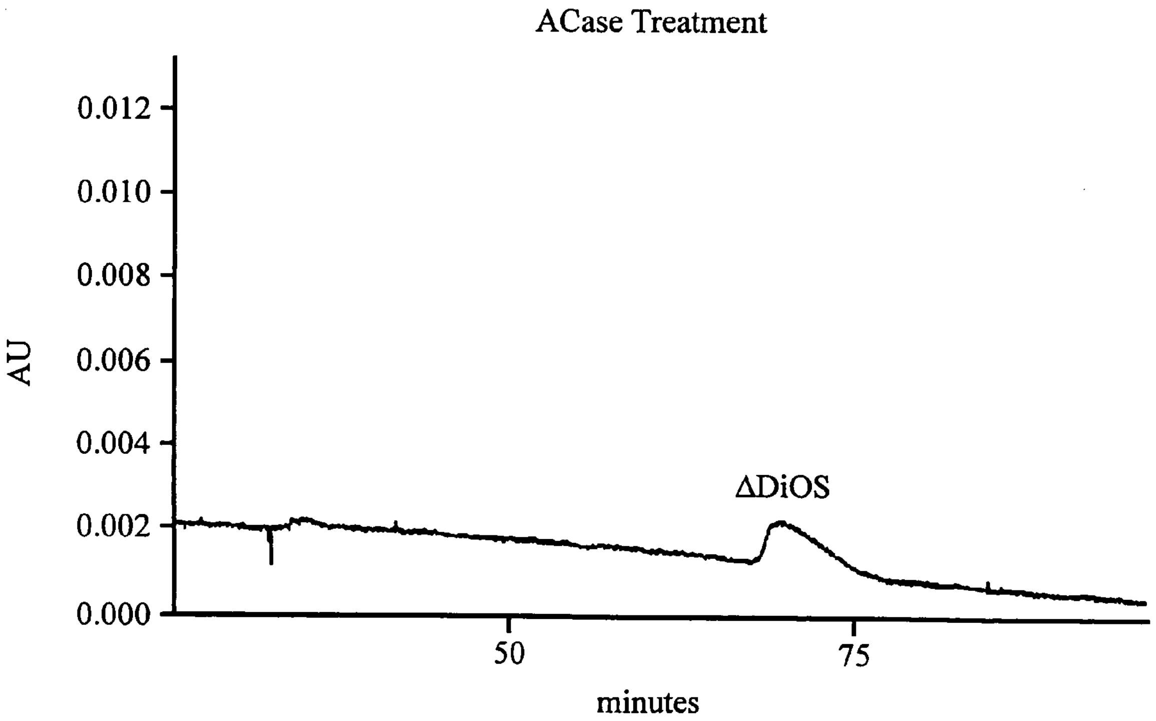
FIG. 10. Disaccharide Composition Analysis—Samples were dissolved in 10 μl of 50 mM Tris-HCl and 60 mM sodium acetate buffer, pH 8, and 20 mU Chondroitinase AC was added separately. The digestions were kept in a 37° C. water bath overnight. The enzymes were deactivated by boiling for 2 min. The experiments were performed with a capillary electrophoresis P/ACE 5500 System (Beckman Instruments, Fullerton, Calif.) at a constant capillary temperature of 18° C. with a potential of −22 kV by UV absorbance at 232 nm. The electropherograms were acquired using the system Gold software package (Beckman Instruments, Fullerton, Calif.). Separation and analysis were carried out in a reversed polarity mode using a fused silica (externally coated except where the tube passed through the detector) capillary tube (50 μm inner diameter, 360 μm outer diameter, 57 cm long, and 49 cm effective length). Prior to every run, the capillary was conditioned with 0.5M NaOH (1 min, 20 psi) and rinsed (1 min, 20 psi) with separation buffer (20 mM $H_3PO_4$ adjusted to pH 3.5 with saturated dibasic sodium phosphate). Samples were applied by pressure injection 25 s at 0.5 psi. Standards of all potential chondroitin oligosaccharides were used to calibrate the capillary. The unsulfated disaccharide, ΔDiOS, was observed in digests of Type F polymer. Thus, the native polymer of Type F is an unsulfated chondroitin.

The ion exchange profile of the chondroitin sulfate hydrolyzate was indistinguishable from the Type F hydrolyzate; mixing experiments demonstrated that the component peaks migrated identically. No other sugars were detected in the Type F polymer including glucosamine, mannose, galactose, glucose, and fucose. Hydrolyzates of the HA and heparin standards clearly contained glucosamine but not galactosamine. Preliminary NMR studies are consistent with the hypothesis that the amino sugar of the Type F polymer is present in an acetylated form (NAc $CH_3$ chemical shift at 2.02 ppm in $D_2O$; University of Georgia Complex Carbohydrate Research Center) (FIG. 8). Disaccharide analysis of the chondroitin from Type F is of the correct mass and charge expected to be derived from unsulfated chondroitin (FIGS. 9 and 10). This process involves cleaving the polymer with chondroitinase, separating products by capillary electrophoresis. The retention time is compared to authentic standards. Mass was measured by mass spectrometry; in this size range, exact masses to within 1 Da are measured.

Molecular Cloning of the Type F *P. multocida* Capsular Locus—PCR products were obtained utilizing Type F chromosomal DNA as a template and various oligonucleotide primers corresponding to the Type A capsule locus. A 3.6 kb PCR product, which contained large portions of the Type F KfaA homolog (a putative polysaccharide transporter of *E. coli*) and the putative pmCS gene, was used as a hybridization probe to obtain an intact *P. multocida* capsular locus from a lambda library. Two positively hybridizing plaques were found after screening about $10^4$ plaques, and these phage were converted into plasmids. We found that both plasmids contained a novel open reading frame of 965 residues, which we named pmCS, that was highly homologous to the Type A HA synthase, pmHAS (FIG. 1). The level of identity was about 87% at both the DNA and protein levels. The differences in amino acid sequence were mainly localized to several regions of the polypeptide in the amino terminal half of the molecules. There is an excellent overall alignment of the enzymes except for a 7-residue insertion in the pmHAS sequence in the position corresponding to residue 53 of the pmCS sequence.

The central portion of both the pmCS and the pmHAS polypeptides (residues 430-530) is most homologous to bacterial glycosyltransferases from a wide variety of genera, including *Streptococcus, Vibric, Neisseria* and *Staphylococcus,* that form exopolysaccharides or the carbohydrate portions of lipopolysaccharides. The some of the most notable sequence similarities are the DGSTD and the DxDD motifs. Directly downstream of the pmCS gene a putative UDP-glucose dehydrogenase gene was identified. Therefore, the relative gene order [KfaA homolog—polysaccharide synthase gene—UDP-glucose dehydrogenase gene] in this portion of the *Pasteurella* Type F capsule operon is the same as that found in Type A.

Heterologous Expression of a Functional *P. multocida* Chondroitin Synthase—Western blot analysis using a monospecific antipeptide antibody was used to detect the production of $pmCS^{1-704}$ or $pmHAS^{1-703}$ polypeptide (FIG. 2). Both enzymes contain a sequence that corresponds exactly to the synthetic peptide used to generate the antibody. Extracts derived from *E. coli* Tuner cells containing the $pmCS^{1-704}$ plasmid contained an immunoreactive band of the appropriate size (i.e. predicted to be 80 kDa), but this band was not present in samples from cells with the vector alone control. The use of soluble $pmCS^{1-704}$ protein provided increased expression levels and facilitated preparation of enzyme in comparison to use of the native-length membrane protein.

Extracts derived from *E. coli* Tuner cells containing the $pmCS^{1-704}$ plasmid, but not samples from cells with the vector alone, synthesized polymer in vitro when supplied with both UDP-GlcUA and UDP-GalNAc simultaneously (Table 3).

TABLE 3

Transferase Specificity of Recombinant $pmCS^{1-704}$ for Sugar Nucleotides. Crude bPer extract (150 μg of total protein) was incubated in 50 μl of assay buffer containing 0.5 μg of chondroitin oligosaccharide acceptor for 20 min either with UDP-[$^{14}$C]GlcUA or UDP-[$^{3}$H]GalNAc. The radiolabeled sugar (300 μM, 0.04 μCi) was used in the presence of the indicated second unlabeled sugar nucleotide (600 μM). The incorporation into polymer was assessed by paper chromatography. The relative percentage of incorporation in comparison to the assay containing the authentic precursor (set to 100%) is shown in parentheses. A representative experiment is shown. The recombinant $pmCS^{1-704}$ incorporated only the authentic chondroitin precursors into polysaccharide.

| | Incorporation of first sugar | |
|---|---|---|
| Second sugar nucleotide Present | [$^{14}$C]GlcUA | [$^{3}$H]GalNAc |
| | dpm (%) | |
| None | 60 (0.9) | 250 (7.5) |
| UDP-GlcUA | ND* | 3,310 (100) |
| UDP-GalUA | ND | 315 (9.5) |
| UDP-GlcNAc | 6,590 (100) | ND |
| UDP-GlcNAc | 85 (1.5) | ND |
| UDP-Glc | 60 (0.9) | 370 (11) |

*ND, not determined.

No incorporation of radiolabeled [$^{14}$C]GlcUA into polymer was observed if UDP-GalNAc was omitted, or if UDP-GlcNAc was substituted for UDP-GalNAc. Conversely, in experiments using UDP-[$^{3}$H]GalNAc, substantial incorporation of radiolabel into polymer was only noted when UDP-GlcUA was also present. UDP-GalUA or UDP-Glc did not substitute for UDP-GlcUA. No polymerization or transferase activity was detected if the divalent metal ions were chelated with EDTA. The addition of the chondroitin oligosaccharide acceptor increased sugar incorporation catalyzed by $pmCS^{1-704}$ at least 50- to 100-fold in comparison to parallel reactions without acceptor in analogy to observations of pmHAS.

Figure 3:
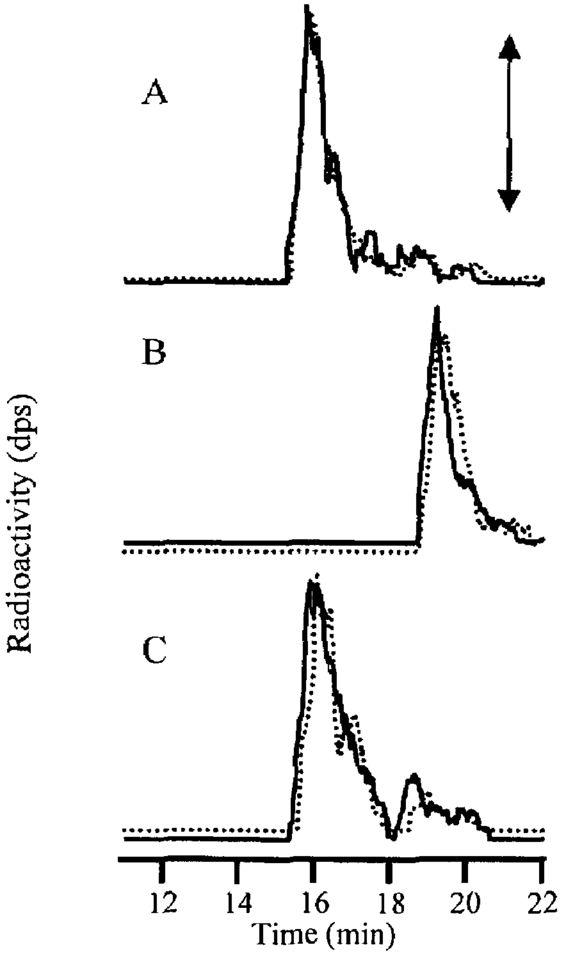
FIG. 3. Gel Filtration Analysis of Radiolabeled Polymer Synthesized in vitro. The $pmCS^{1-704}$ extract (1 mg total protein) was incubated with chondroitin acceptor oligosaccharide (5 μg), UDP-[$^{14}$C]GlcUA and UDP-[$^{3}$H]GalNAc (580 μM, 0.16 μCi each) in a reaction volume of 200 μl for 30 min. The reaction product was split into five aliquots and treated with various GAG glycosidases as described in Experimental Procedures. Portions (60%) of the samples were then analyzed on the PolySep column (calibration elution times in minutes: void volume, 12.7; 580 kDa dextran, 15.4 kDa dextran, 16.0, totally included volume, 19.3 min). Radioactivity ($^{14}$C, solid line; $^{3}$H, dotted line) measured by the in-line detector is presented as disintegrations per second (dps). The double-headed arrow corresponds to a response of 20 dps. A, untreated polymer, peak 15.9 min; B, *Flavobacterium* chondroitinase AC lyase-treated polymer, peak, 19.2 min; C, HA lyase-treated polymer, peak 15.9 min. The polymer peak with a size of ~100 to 400 kDa contained both radiolabeled sugars at a 1:1 ratio and was degraded only by the appropriate enzyme, chondroitin AC lyase.

Analysis by gel filtration chromatography indicated that recombinant pmCS produced polymer chains of $10^3$=(1,000) monosaccharides long (100 to 400 kDa) in vitro. Radioactivity from both labeled GlcUA and GalNAc sugars co-migrated as a single peak (FIG. 3A). No radiolabel was incorporated into high molecular weight polymer if both UDP-sugars were not present during the assay. The identity of the polymer as chondroitin was verified by its sensitivity to *Flavobacterium* or *Proteus* chondroitin AC lyase (FIG. 3B) and its resistance to the action of *Streptomyces* HA lyase (FIG. 3C).

Figure 4:
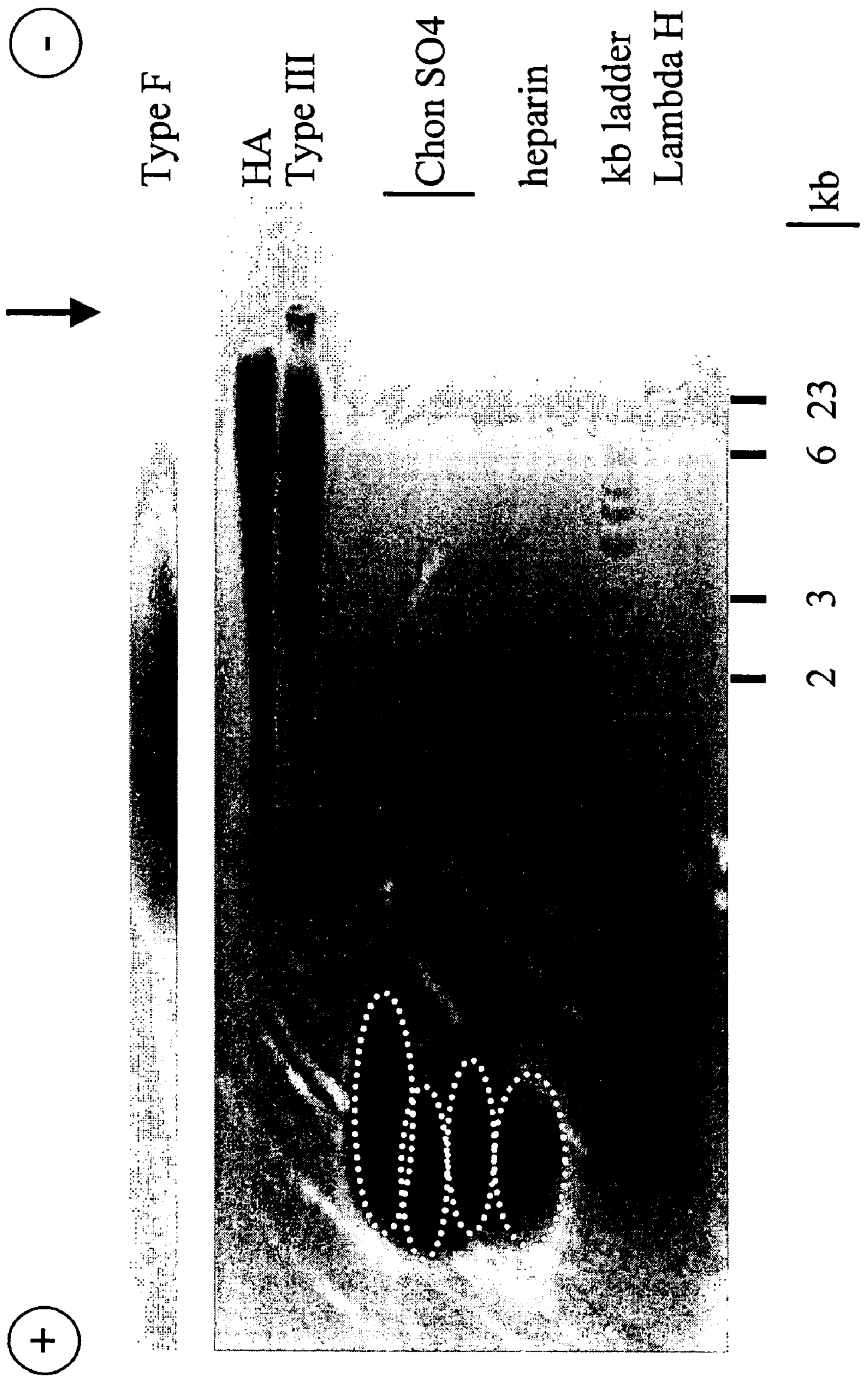
FIG. 4. Gel Electrophoresis Analysis of Polysaccharides. Various polymers were separated by their mass/charge ratio on 0.8% agarose gels in a 1×TAE (tris acetate EDTA) buffer system. About 9 ug of polymer were loaded per lane and separated using a field of 0.8 volts/cm. Lanes: Type F, native polymer from *Pasteurella multocida* Type F; HA, hyaluronic acid; Type III, *Streptococcus pneumoniae* type 3 capsular polymer; Chon SO4, Chondroitin sulfate C,B,A—from left to right [note: marked in white dotted circle]; heparin, porcine heparin; kb ladder, kilobase DNA ladder standard; Lambda H, HindIII digest of lambda virus DNA standard. Sizes of select DNA standards are marked in kilobases (kb). After electrophoresis, the gel was stained with the dye Stains-All (Sigma; 0.05% in 50% ethanol, w/v) for 2 hours, then destained in water. Type F polymer runs slower than chondroitin sulfate polymers because it is larger and not as highly charged (missing the extra charges of sulfates). The staining color for HA, Type III and Type F polymers is blue, but chondroitin sulfate stains purple. The Type F polysaccharide is a novel large unsulfated chondroitin chain, the first report of this polymer.

Analysis of the native Type F polymer by agarose gel electrophoresis also shows that high molecular weight polymer is made by bacteria in vivo (FIG. 4). The Type F polymer was visualized by stains. All staining an 0.8% agarose gel run in 1×TAE system. HA and Type F both stained blue while DNA and chondroitin sulfate stained purple and Heparin stained yellow. The Type F polymer is smaller than HA, but still forms very large chains of about 50 to about 150 KDa.

*P. multocida* Type F produces a chondroitin capsule. The glycosyltransferase responsible for polymerizing the chondroitin backbone component of the capsular polysaccharide has also been cloned. The pmCS enzyme appears to be a close homolog of the pmHAS enzyme. Recently, it was determined that the pmHAS enzyme contains two active sites in a single polypeptide by generating mutants that transfer only GlcUA or only GlcNAc. Mixing the two different mutant proteins reconstituted the HA synthase activity. It is likely that one domain, called A1, is responsible for GlcNAc transfer and the other domain, called A2, is responsible for GlcUA transfer. Comparison of the pmHAS and the pmCS sequences reveals that the majority of the sequence differences exist in the A1 domain. The pmCS enzyme transfers a different hexosamine, GalNAc, thus being consistent with the proposed two-domain structure for pmHAS.

The pmHAS protein was also hypothesized to interact with a putative polysaccharide transporter system or a membrane-bound partner via its carboxyl terminus because deletion of residues 704 to 972 from the native-length enzyme resulted in the formation of a soluble enzyme. However, no substantial membrane-associated or hydrophobic regions are predicted to reside in this sequence. As pmHAS and pmCS are highly homologous in this region, which is not essential for their glycosyltransferase activities, it is quite likely that the carboxyl terminus contains domains or motifs required for interacting with the polysaccharide transport machinery or a membrane-bound partner in vivo. The evolutionary relationship between Type A and Type F *P. multocida* strains has not yet been delineated. Both organisms are widespread causative agents of fowl cholera, but many more isolates from diseased birds in North America are Type A microbes with HA capsules. It is likely that the progenitor of the two distinct capsular types had either a chondroitin synthase like or a HAS-like gene. The specificity of this ancestral enzyme may have changed after a few mutations resulting in the appearance of another capsular type. Apparently, the sugar transfer specificity is rather selective since neither recombinant pmCS nor pmHAS misincorporate the inappropriate hexosamine into polymer in vitro. Some Gram-negative bacteria (e.g. *E. coli*) possess an UDP-GlcNAc/UDP-GalNAc epimerase, therefore the hexosamine precursor either for HA or for chondroitin could have been available for polysaccharide biosynthesis without the need to gain an auxiliary metabolic enzyme simultaneously. Typically the UDP-glucose dehydrogenase, the enzyme that forms the UDP-GlcUA precursor, is found in Gram-negative bacteria only if the microbe possesses a GlcUA-containing polymer or glycoconjugate. In both Type A and Type F *P. multocida,* the UDP-glucose dehydrogenase gene is directly downstream of the GAG synthase.

The relationship between the bacterial chondroitin synthase and the putative mammalian counterpart is unclear. No similar vertebrate proteins are deposited in the database as yet. Both bacterial pmCS and the vertebrate chondroitin synthase utilize UDP-sugars to extend acceptor carbohydrates in vitro. In most cases, the mammalian enzyme in cell-free extracts, however, does not produce long chondroitin chains and only the half-reaction (e.g. adding a single GlcUA to a GalNAc-terminated oligosaccharide or vice versa) is readily observed in vitro. In vertebrate tissues, other enzymes modify chondroitin extensively by sulfation and/or epimerization. The discovery and the characterization of pmCS will assist the further study of the rather recalcitrant mammalian chondroitin synthase enzymes.

Thus, it should be apparent that there has been provided in accordance with the present invention a purified nucleic acid segment having a coding region encoding enzymatically active chondroitin synthase, methods of producing chondroitin from the pmCS gene, and the use of chondroitin produced from a chondroitin synthase encoded by the pmCS gene, that fully satisfies the objectives and advantages set forth above. Although the invention has been described in conjunction with specific embodiments thereof, it is evident that many alternatives, modifications, and variations will be apparent to those skilled in the art.

Accordingly, it is intended to embrace all such alternatives, modifications, and variations that fall within the spirit and broad scope of the appended claims.

What I claim is:

1. A purified nucleic acid segment having a coding region encoding enzymatically active chondroitin synthase, wherein the enzymatically active chondroitin synthase is a single protein that catalyzes the incorporation of both UDP-GlcA and UDP-GalNAc to form a chondroitin molecule, and wherein the purified nucleic acid segment comprises at least one of:

(a) the nucleotide sequence in accordance with SEQ ID NO:3; and (b) a nucleotide sequence encoding the amino acid sequence of SEQ ID NO:4.

2. A recombinant vector comprising the purified nucleic acid segment of claim 1.

3. The recombinant vector of claim 2, wherein the recombinant vector is selected from the group consisting of a plasmid, cosmid, phage, integrated cassette and virus vector.

4. The recombinant vector of claim 2, further comprising a promoter operatively linked to the coding region encoding enzymatically active chondroitin synthase.

5. A recombinant host cell comprising the recombinant vector of claim 2.

6. The recombinant host cell of claim 5, wherein the host cell produces chondroitin.

7. The recombinant host cell of claim 5, wherein the recombinant host cell is a prokaryotic cell.

8. The recombinant host cell of claim 5, wherein the recombinant host cell is a eukaryotic cell cultured in vitro.

9. A purified nucleic acid segment having a coding region encoding enzymatically active chondroitin synthase, wherein the enzymatically active chondroitin synthase is a single protein that catalyzes the incorporation of both UDP-GlcA and UDP-GalNAc to form a chondroitin molecule, and wherein the purified nucleic acid segment has at least 90% identity to SEQ ID NO:3.

10. A recombinant vector comprising the purified nucleic acid segment of claim 9.

11. The recombinant vector of claim 10, wherein the recombinant vector is selected from the group consisting of a plasmid, cosmid, phage, integrated cassette and virus vector.

12. The recombinant vector of claim 10, further comprising a promoter operatively linked to the coding region encoding enzymatically active chondroitin synthase.

13. A recombinant host cell comprising the recombinant vector of claim 10.

14. The recombinant host cell of claim 13, wherein the host cell produces chondroitin.

15. The recombinant host cell of claim 13, wherein the recombinant host cell is a prokaryotic cell.

16. The recombinant host cell of claim 13, wherein the recombinant host cell is a eukaryotic cell cultured in vitro.

* * * * *

UNITED STATES PATENT AND TRADEMARK OFFICE

CERTIFICATE OF CORRECTION

PATENT NO. : 7,569,386 B2
APPLICATION NO. : 11/042530
DATED : August 4, 2009
INVENTOR(S) : Paul L. DeAngelis It is certified that error appears in the above-identified patent and that said Letters Patent is hereby corrected as shown below:

Column 24, line 51, Table 3: Delete "UDP - GlcNAc" which is listed below "UDP - GalUA" and replace with
-- UDP - GalNAc --.

Signed and Sealed this

Eighth Day of September, 2009

David J. Kappos

David J. Kappos
*Director of the United States Patent and Trademark Office*

SEQUENCE LISTING

```
<160> NUMBER OF SEQ ID NOS: 7

<210> SEQ ID NO 1
<211> LENGTH: 2979
<212> TYPE: DNA
<213> ORGANISM: Pasteurella multocida

<400> SEQUENCE: 1

ttataaactg attaaagaag gtaaacgatt caagcaaggt taatttttaa aggaaagaaa      60

atgaatacat tatcacaagc aataaaagca tataacagca atgactatga attagcactc     120

aaattatttg agaagtctgc tgaaacctac gggcgaaaaa tcgttgaatt ccaaattatc     180
```

-continued

```
aaatgtaaag aaaaactctc gaccaattct tatgtaagtg aagataaaaa aaacagtgtt    240
tgcgatagct cattagatat cgcaacacag ctcttacttt ccaacgtaaa aaaattaact    300
ctatccgaat cagaaaaaaa cagtttaaaa aataaatgga aatctatcac tgggaaaaaa    360
tcggagaacg cagaaatcag aaaggtggaa ctagtaccca aagattttcc taaagatctt    420
gttcttgctc cattgccaga tcatgttaat gattttacat ggtacaaaaa tcgaaaaaaa    480
agcttaggta taaagcctgt aaataagaat atcggtcttt ctattattat tcctacattt    540
aatcgtagcc gtattttaga tataacgtta gcctgtttgg tcaatcagaa aacaaactac    600
ccatttgaag tcgttgttgc agatgatggt agtaaggaaa acttacttac cattgtgcaa    660
aaatacgaac aaaaacttga cataaagtat gtaagacaaa aagattatgg atatcaattg    720
tgtgcagtca gaaacttagg tttacgtaca gcaaagtatg attttgtctc gattctagac    780
tgcgatatgg caccacaaca attatgggtt cattcttatc ttacagaact attagaagac    840
aatgatattg ttttaattgg acctagaaaa tatgtggata ctcataatat taccgcagaa    900
caattcctta acgatccata tttaatagaa tcactacctg aaaccgctac aaataacaat    960
ccttcgatta catcaaaagg aaatatatcg ttggattgga gattagaaca tttcaaaaaa   1020
accgataatc tacgtctatg tgattctccg tttcgttatt ttgttgcggg taatgttgca   1080
ttttctaaag aatggctaaa taaagtaggt tggttcgatg aagaatttaa tcattggggg   1140
ggcgaagatg tagaatttgg ttacagatta tttgccaaag gctgtttttt cagagtaatt   1200
gacggcggaa tggccatcca tcaagaacca cctggtaaag aaaatgaaac agaacgcgaa   1260
gctggtaaaa gtattacgct taaaattgtg aaagaaaagg taccttacat ctatagaaag   1320
cttttaccaa tagaagattc acatattcat agaatacctt tagtttctat ttatatcccc   1380
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccatttttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatatgttaa aagatcttaa actcattcaa   2160
aataaagatg ccaaaatcgc agtcagtatt ttctatccca atacattaaa cggcttagtg   2220
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcattttttg ataatcatga cagcctattc gttaaaaatg acagctatgc ttatatgaaa   2520
aaatatgatg tcggcatgaa tttctcagca ttaacacatg attggatcga gaaaatcaat   2580
```

-continued

```
gcgcatccac catttaaaaa gctgattaaa acctatttta atgacaatga cttaagaagt   2640

atgaatgtga aaggggcatc acaaggtatg tttatgaagt atgcgctacc gcatgagctt   2700

ctgacgatta ttaaagaagt catcacatcc tgccaatcaa ttgatagtgt gccagaatat   2760

aacactgagg atatttggtt ccaatttgca cttttaatct tagaaaagaa aaccggccat   2820

gtatttaata aaacatcgac cctgacttat atgccttggg aacgaaaatt acaatggaca   2880

aatgaacaaa ttcaaagtgc aaaaaaaggc gaaaatatcc ccgttaacaa gttcattatt   2940

aatagtataa cgctataaaa catttgcatt ttattaaaa                          2979


<210> SEQ ID NO 2
<211> LENGTH: 965
<212> TYPE: PRT
<213> ORGANISM: Pasteurella multocida

<400> SEQUENCE: 2

Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Asn Pro Ser Ile Thr
    290                 295                 300
```

-continued

```
Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Val Ala
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
    370                 375                 380

Ala Ile His Gln Glu Pro Pro Gly Lys Glu Asn Glu Thr Glu Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620

Ile Cys Tyr Asn Arg Val Leu His Gly Asp Asn Thr Ser Ile Lys Lys
625                 630                 635                 640

Leu Gly Ile Gln Lys Lys Asn His Phe Val Val Val Asn Gln Ser Leu
                645                 650                 655

Asn Arg Gln Gly Ile Asn Tyr Tyr Asn Tyr Asp Lys Phe Asp Asp Leu
            660                 665                 670

Asp Glu Ser Arg Lys Tyr Ile Phe Asn Lys Thr Ala Glu Tyr Gln Glu
        675                 680                 685

Glu Met Asp Met Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720
```

-continued

```
Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
            740                 745                 750

Ile Leu Ala Phe Tyr His Lys His Gln Val Asn Ile Leu Leu Asn Asn
        755                 760                 765

Asp Ile Ser Tyr Tyr Thr Ser Asn Arg Leu Ile Lys Thr Glu Ala His
    770                 775                 780

Leu Ser Asn Ile Asn Lys Leu Ser Gln Leu Asn Leu Asn Cys Glu Tyr
785                 790                 795                 800

Ile Ile Phe Asp Asn His Asp Ser Leu Phe Val Lys Asn Asp Ser Tyr
                805                 810                 815

Ala Tyr Met Lys Lys Tyr Asp Val Gly Met Asn Phe Ser Ala Leu Thr
            820                 825                 830

His Asp Trp Ile Glu Lys Ile Asn Ala His Pro Pro Phe Lys Lys Leu
        835                 840                 845

Ile Lys Thr Tyr Phe Asn Asp Asn Asp Leu Arg Ser Met Asn Val Lys
    850                 855                 860

Gly Ala Ser Gln Gly Met Phe Met Lys Tyr Ala Leu Pro His Glu Leu
865                 870                 875                 880

Leu Thr Ile Ile Lys Glu Val Ile Thr Ser Cys Gln Ser Ile Asp Ser
                885                 890                 895

Val Pro Glu Tyr Asn Thr Glu Asp Ile Trp Phe Gln Phe Ala Leu Leu
            900                 905                 910

Ile Leu Glu Lys Lys Thr Gly His Val Phe Asn Lys Thr Ser Thr Leu
        915                 920                 925

Thr Tyr Met Pro Trp Glu Arg Lys Leu Gln Trp Thr Asn Glu Gln Ile
    930                 935                 940

Gln Ser Ala Lys Lys Gly Glu Asn Ile Pro Val Asn Lys Phe Ile Ile
945                 950                 955                 960

Asn Ser Ile Thr Leu
                965


<210> SEQ ID NO 3
<211> LENGTH: 2979
<212> TYPE: DNA
<213> ORGANISM: Pasteurella multocida

<400> SEQUENCE: 3

ttataaactg attaaagaag gtaaacgatt caagcaaggt taatttttaa aggaaagaaa      60

atgaatacat tatcacaagc aataaaagca tataacagca atgactatga attagcactc     120

aaattatttg agaagtctgc tgaaacctac gggcgaaaaa tcgttgaatt ccaaattatc     180

aaatgtaaag aaaaactctc gaccaattct tatgtaagtg aagataaaaa aaacagtgtt     240

tgcgatagct cattagatat cgcaacacag ctcttacttt ccaacgtaaa aaaattaact     300

ctatccgaat cagaaaaaaa cagtttaaaa aataaatgga aatctatcac tgggaaaaaa     360

tcggagaacg cagaaatcag aaaggtggaa ctagtaccca aagattttcc taaagatctt     420

gttcttgctc cattgccaga tcatgttaat gattttacat ggtacaaaaa tcgaaaaaaa     480

agcttaggta taaagcctgt aaataagaat atcggtcttt ctattattat tcctacattt     540

aatcgtagcc gtattttaga tataacgtta gcctgtttgg tcaatcagaa aacaaactac     600

ccatttgaag tcgttgttgc agatgatggt agtaaggaaa acttacttac cattgtgcaa     660

aaatacgaac aaaaacttga cataaagtat gtaagacaaa aagattatgg atatcaattg     720
```

-continued

```
tgtgcagtca gaaacttagg tttacgtaca gcaaagtatg attttgtctc gattctagac    780
tgcgatatgg caccacaaca attatgggtt cattcttatc ttacagaact attagaagac    840
aatgatattg ttttaattgg acctagaaaa tatgtggata ctcataatat taccgcagaa    900
caattcctta acgatccata tttaatagaa tcactacctg aaaccgctac aaataacaat    960
ccttcgatta catcaaaagg aaatatatcg ttggattgga gattagaaca tttcaaaaaa   1020
accgataatc tacgtctatg tgattctccg tttcgttatt ttagttgcgg taatgttgca   1080
ttttctaaag aatggctaaa taaagtaggt tggttcgatg aagaatttaa tcattggggg   1140
ggcgaagatg tagaatttgg ttacagatta tttgccaaag gctgtttttt cagagtaatt   1200
gacggcggaa tggcatacca tcaagaacca cctggtaaag aaaatgaaac agaccgcgaa   1260
gctggtaaaa gtattacgct taaaattgtg aaagaaaagg taccttacat ctatagaaag   1320
cttttaccaa tagaagattc acatattcat agaatacctt tagtttctat ttatatcccc   1380
gcttataact gtgcaaatta tattcaaaga tgtgtagata gtgctcttaa tcaaactgtt   1440
gtcgatctcg aggtttgtat ttgtaacgat ggttcaacag ataatacctt agaagtgatc   1500
aataagcttt atggtaataa tcctagggta cgcatcatgt ctaaaccaaa tggcggaata   1560
gcctcagcat caaatgcagc cgtttctttt gctaaaggtt attacattgg gcagttagat   1620
tcagatgatt atcttgagcc tgatgcagtt gaactgtgtt taaaagaatt tttaaaagat   1680
aaaacgctag cttgtgttta taccactaat agaaacgtca atccggatgg tagcttaatc   1740
gctaatggtt acaattggcc agaattttca cgagaaaaac tcacaacggc tatgattgct   1800
caccatttta gaatgtttac gattagagct tggcatttaa cggatggatt taacgaaaat   1860
attgaaaacg ccgtggatta tgacatgttc cttaaactca gtgaagttgg aaaatttaaa   1920
catcttaata aaatctgcta taaccgcgta ttacatggtg ataacacatc cattaagaaa   1980
ctcggcattc aaaagaaaaa ccattttgtt gtagtcaatc agtcattaaa tagacaaggc   2040
atcaattatt ataattatga caaatttgat gatttagatg aaagtagaaa gtatatcttc   2100
aataaaaccg ctgaatatca agaagaaatg gatattttaa aagatcttaa actcattcaa   2160
aataaagatg ccaaaatcgc agtcagtatt ttctatccca atacattaaa cggcttagtg   2220
aaaaaactaa acaatattat tgaatataat aaaaatatat tcgttattat tctacatgtt   2280
gataagaatc atcttacacc agacatcaaa aaagaaatat tggctttcta tcataagcac   2340
caagtgaata ttttactaaa taatgacatc tcatattaca cgagtaatag actaataaaa   2400
actgaggcac atttaagtaa tattaataaa ttaagtcagt taaatctaaa ttgtgaatac   2460
atcatttttg ataatcatga cagcctattc gttaaaaatg acagctatgc ttatatgaaa   2520
aaatatgatg tcggcatgaa tttctcagca ttaacacatg attggatcga gaaaatcaat   2580
gcgcatccac catttaaaaa gctgattaaa acctatttta atgacaatga cttaagaagt   2640
atgaatgtga aaggggcatc acaaggtatg tttatgaagt atgcgctacc gcatgagctt   2700
ctgacgatta ttaaagaagt catcacatcc tgccaatcaa ttgatagtgt gccagaatat   2760
aacactgagg atatttggtt ccaatttgca cttttaatct tagaaaagaa aaccggccat   2820
gtatttaata aaacatcgac cctgacttat atgccttggg aacgaaaatt acaatggaca   2880
aatgaacaaa ttcaaagtgc aaaaaaaggc gaaaatatcc ccgttaacaa gttcattatt   2940
aatagtataa cgctataaaa catttgcatt ttattaaaa                          2979
```

<210> SEQ ID NO 4

-continued

<211> LENGTH: 965
<212> TYPE: PRT
<213> ORGANISM: Pasteurella multocida

<400> SEQUENCE: 4

```
Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Leu Ser Asn Val Lys Lys Leu Thr
65                  70                  75                  80

Leu Ser Glu Ser Glu Lys Asn Ser Leu Lys Asn Lys Trp Lys Ser Ile
                85                  90                  95

Thr Gly Lys Lys Ser Glu Asn Ala Glu Ile Arg Lys Val Glu Leu Val
            100                 105                 110

Pro Lys Asp Phe Pro Lys Asp Leu Val Leu Ala Pro Leu Pro Asp His
        115                 120                 125

Val Asn Asp Phe Thr Trp Tyr Lys Asn Arg Lys Lys Ser Leu Gly Ile
    130                 135                 140

Lys Pro Val Asn Lys Asn Ile Gly Leu Ser Ile Ile Ile Pro Thr Phe
145                 150                 155                 160

Asn Arg Ser Arg Ile Leu Asp Ile Thr Leu Ala Cys Leu Val Asn Gln
                165                 170                 175

Lys Thr Asn Tyr Pro Phe Glu Val Val Val Ala Asp Asp Gly Ser Lys
            180                 185                 190

Glu Asn Leu Leu Thr Ile Val Gln Lys Tyr Glu Gln Lys Leu Asp Ile
        195                 200                 205

Lys Tyr Val Arg Gln Lys Asp Tyr Gly Tyr Gln Leu Cys Ala Val Arg
    210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Asn Pro Ser Ile Thr
    290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
    370                 375                 380

Ala Tyr His Gln Glu Pro Pro Gly Lys Glu Asn Glu Thr Asp Arg Glu
```

-continued

```
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
    450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Asp Tyr Leu Glu Pro Asp
        515                 520                 525

Ala Val Glu Leu Cys Leu Lys Glu Phe Leu Lys Asp Lys Thr Leu Ala
    530                 535                 540

Cys Val Tyr Thr Thr Asn Arg Asn Val Asn Pro Asp Gly Ser Leu Ile
545                 550                 555                 560

Ala Asn Gly Tyr Asn Trp Pro Glu Phe Ser Arg Glu Lys Leu Thr Thr
                565                 570                 575

Ala Met Ile Ala His His Phe Arg Met Phe Thr Ile Arg Ala Trp His
            580                 585                 590

Leu Thr Asp Gly Phe Asn Glu Asn Ile Glu Asn Ala Val Asp Tyr Asp
        595                 600                 605

Met Phe Leu Lys Leu Ser Glu Val Gly Lys Phe Lys His Leu Asn Lys
    610                 615                 620

Ile Cys Tyr Asn Arg Val Leu His Gly Asp Asn Thr Ser Ile Lys Lys
625                 630                 635                 640

Leu Gly Ile Gln Lys Lys Asn His Phe Val Val Val Asn Gln Ser Leu
                645                 650                 655

Asn Arg Gln Gly Ile Asn Tyr Tyr Asn Tyr Asp Lys Phe Asp Asp Leu
            660                 665                 670

Asp Glu Ser Arg Lys Tyr Ile Phe Asn Lys Thr Ala Glu Tyr Gln Glu
        675                 680                 685

Glu Met Asp Ile Leu Lys Asp Leu Lys Leu Ile Gln Asn Lys Asp Ala
    690                 695                 700

Lys Ile Ala Val Ser Ile Phe Tyr Pro Asn Thr Leu Asn Gly Leu Val
705                 710                 715                 720

Lys Lys Leu Asn Asn Ile Ile Glu Tyr Asn Lys Asn Ile Phe Val Ile
                725                 730                 735

Ile Leu His Val Asp Lys Asn His Leu Thr Pro Asp Ile Lys Lys Glu
            740                 745                 750

Ile Leu Ala Phe Tyr His Lys His Gln Val Asn Ile Leu Leu Asn Asn
        755                 760                 765

Asp Ile Ser Tyr Tyr Thr Ser Asn Arg Leu Ile Lys Thr Glu Ala His
    770                 775                 780

Leu Ser Asn Ile Asn Lys Leu Ser Gln Leu Asn Leu Asn Cys Glu Tyr
785                 790                 795                 800
```

-continued

```
Ile Ile Phe Asp Asn His Asp Ser Leu Phe Val Lys Asn Asp Ser Tyr
                805                 810                 815

Ala Tyr Met Lys Lys Tyr Asp Val Gly Met Asn Phe Ser Ala Leu Thr
            820                 825                 830

His Asp Trp Ile Glu Lys Ile Asn Ala His Pro Pro Phe Lys Lys Leu
        835                 840                 845

Ile Lys Thr Tyr Phe Asn Asp Asn Asp Leu Arg Ser Met Asn Val Lys
    850                 855                 860

Gly Ala Ser Gln Gly Met Phe Met Lys Tyr Ala Leu Pro His Glu Leu
865                 870                 875                 880

Leu Thr Ile Ile Lys Glu Val Ile Thr Ser Cys Gln Ser Ile Asp Ser
                885                 890                 895

Val Pro Glu Tyr Asn Thr Glu Asp Ile Trp Phe Gln Phe Ala Leu Leu
            900                 905                 910

Ile Leu Glu Lys Lys Thr Gly His Val Phe Asn Lys Thr Ser Thr Leu
        915                 920                 925

Thr Tyr Met Pro Trp Glu Arg Lys Leu Gln Trp Thr Asn Glu Gln Ile
    930                 935                 940

Gln Ser Ala Lys Lys Gly Glu Asn Ile Pro Val Asn Lys Phe Ile Ile
945                 950                 955                 960

Asn Ser Ile Thr Leu
                965


<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5

cactgtctaa ctttattgtt agcc                                            24


<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6

tttttaacga ataggctgtc                                                 20


<210> SEQ ID NO 7
<211> LENGTH: 19
<212> TYPE: PRT
<213> ORGANISM: Artificial Sequence
<220> FEATURE:
<223> OTHER INFORMATION: synthetic peptide corresponding to residues 526
      to 544 of PmHAS protein

<400> SEQUENCE: 7

Leu Asp Ser Asp Asp Tyr Leu Glu Pro Asp Ala Val Glu Leu Cys Leu
1               5                   10                  15

Lys Glu Phe
```